US010588673B2

(12) United States Patent
Fischer et al.

(10) Patent No.: US 10,588,673 B2
(45) Date of Patent: Mar. 17, 2020

(54) MEDICAL INSTRUMENT AND MEDICAL INSTRUMENTARIUM

(71) Applicant: Aesculap AG, Tuttlingen (DE)

(72) Inventors: Kay Fischer, Tuttlingen (DE); Stephan Lindner, Wurmlingen (DE); Sven Krüger, Trossingen (DE)

(73) Assignee: Aesculap AG, Tuttlingen (DE)

( * ) Notice: Subject to any disclaimer, the term of this patent is extended or adjusted under 35 U.S.C. 154(b) by 0 days.

(21) Appl. No.: 15/990,966

(22) Filed: May 29, 2018

(65) Prior Publication Data
US 2018/0271566 A1    Sep. 27, 2018

Related U.S. Application Data

(63) Continuation of application No. PCT/EP2016/079616, filed on Dec. 2, 2016.

(30) Foreign Application Priority Data

Dec. 2, 2015    (DE) .................. 10 2015 120 955

(51) Int. Cl.
*A61B 17/70* (2006.01)
*A61B 90/00* (2016.01)
*A61B 17/00* (2006.01)

(52) U.S. Cl.
CPC ........ *A61B 17/7083* (2013.01); *A61B 17/708* (2013.01); *A61B 17/7032* (2013.01);
(Continued)

(58) Field of Classification Search
CPC ............ A61B 17/7083; A61B 17/7032; A61B 17/7079; A61B 17/708; A61B 17/7085;
(Continued)

(56) References Cited

U.S. PATENT DOCUMENTS 9,211,149 B2    12/2015 Hoefer et al.
9,510,874 B2    12/2016 Krueger
(Continued)

FOREIGN PATENT DOCUMENTS

| DE | 102012107056 | 5/2014 |
|----|--------------|--------|
| DE | 102013108362 | 2/2015 |
| DE | 102013111683 | 4/2015 |

*Primary Examiner* — Pedro Philogene
(74) *Attorney, Agent, or Firm* — Lipsitz & McAllister, LLC

(57) ABSTRACT

The invention relates to a medical instrument for temporarily coupling to at least two instruments, comprising a first coupling device for temporarily coupling to a first shank- or sleeve-shaped instrument and a second coupling device for coupling to a second shank- or sleeve-shaped instrument, wherein the first coupling device and the second coupling device are arranged or formed so as to be pivotable relative to each other, which medical instrument comprises a main body on which the first coupling device is guided and held so as to be pivotable about a point of rotation that in particular is spatially remote from the main body, which medical instrument comprises a first guide device for guiding a movement of the first coupling device along a circular path, wherein the first guide device is arranged or formed at least partially on the main body.

25 Claims, 17 Drawing Sheets

Figure 1:
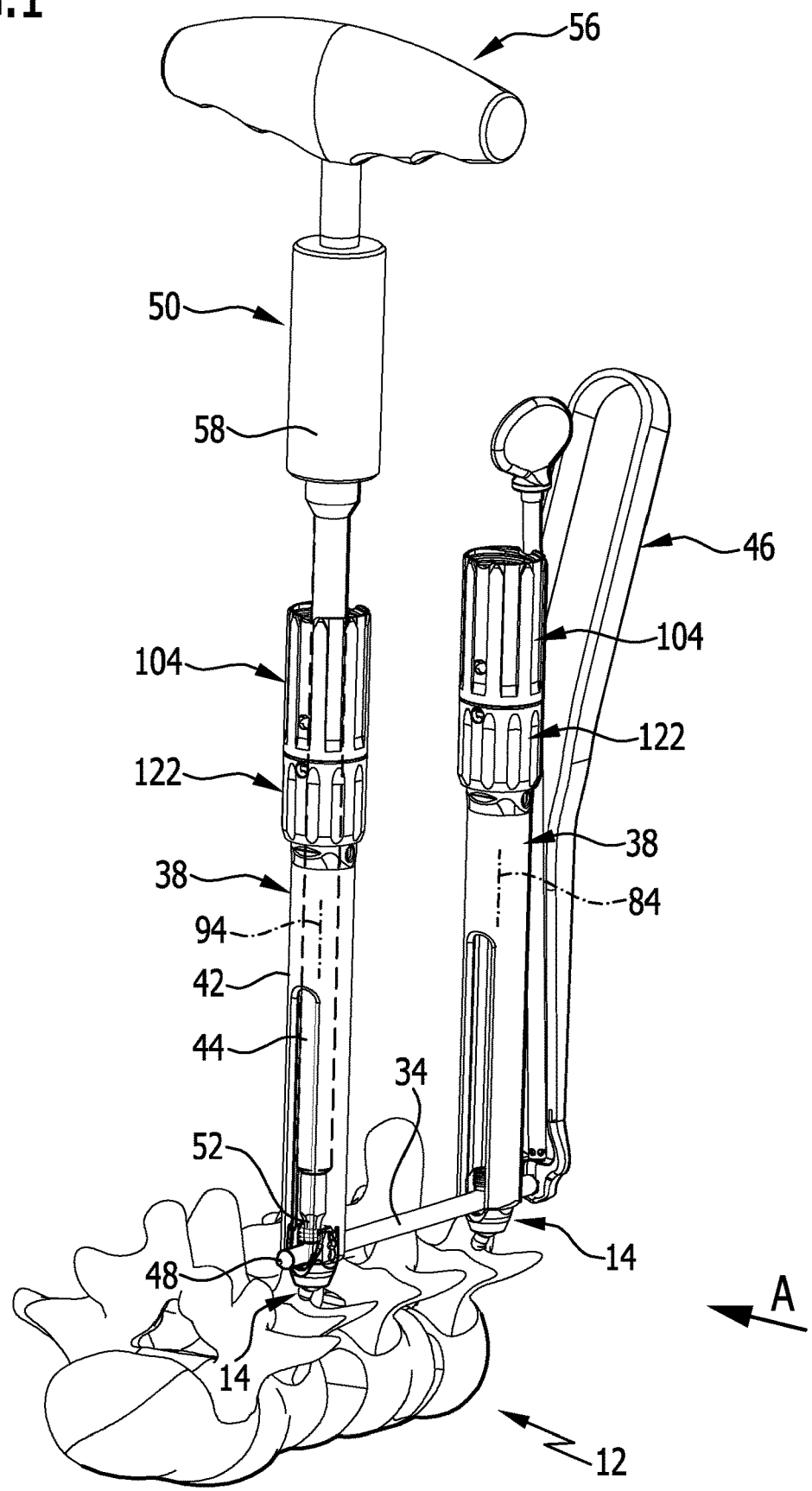

(52) U.S. Cl.
CPC ...... *A61B 17/7079* (2013.01); *A61B 17/7085* (2013.01); *A61B 17/7091* (2013.01); *A61B 17/7037* (2013.01); *A61B 17/7082* (2013.01); *A61B 2017/00477* (2013.01); *A61B 2090/067* (2016.02)

(58) Field of Classification Search
CPC ............ A61B 17/7091; A61B 17/7037; A61B 17/7082; A61B 17/7074; A61B 17/7041; A61B 17/7014; A61B 90/06; A61B 2090/067; A61B 2090/061; A61B 2017/00477
USPC ................ 606/105, 86 A, 102, 246–279
See application file for complete search history.

(56) References Cited

U.S. PATENT DOCUMENTS

| | | | |
|---|---|---|---|
| 9,808,295 B2 | 11/2017 | Peukert et al. | |
| 2008/0077155 A1* | 3/2008 | Diederich | A61B 17/708 606/105 |
| 2012/0226284 A1* | 9/2012 | Sorrenti | A61B 17/025 606/90 |
| 2012/0265212 A1* | 10/2012 | Seck | A61B 17/708 606/102 |
| 2012/0289633 A1* | 11/2012 | Liang | G02F 1/1337 524/104 |
| 2013/0211453 A1 | 8/2013 | Lenke et al. | |
| 2013/0289633 A1 | 10/2013 | Gleeson et al. | |
| 2014/0039567 A1 | 2/2014 | Hoefer et al. | |
| 2014/0107659 A1* | 4/2014 | Walters | A61B 17/7074 606/102 |
| 2015/0039035 A1* | 2/2015 | Kruger | A61B 17/7037 606/264 |
| 2015/0066088 A1* | 3/2015 | Brinkman | A61B 17/7077 606/264 |
| 2015/0112399 A1 | 4/2015 | Peukert et al. | |

* cited by examiner

MEDICAL INSTRUMENT AND MEDICAL INSTRUMENTARIUM

CROSS-REFERENCE TO RELATED APPLICATIONS

This application is a continuation of international application number PCT/EP2016/079616 filed on Dec. 2, 2016 and claims the benefit of German application number 10 2015 120 955.1 filed on Dec. 2, 2015, which are incorporated herein by reference in their entirety and for all purposes.

FIELD OF THE INVENTION

The present invention relates to medical instruments generally, and more specifically to a medical instrument for temporarily coupling to at least two shank- or sleeve-shaped instruments, comprising a first coupling device for temporary coupling to a first shank- or sleeve-shaped instrument and a second coupling device for coupling to a second shank- or sleeve-shaped instrument.

The present invention further relates to medical instrumentaria generally, and more specifically to a medical instrumentarium for implanting a spinal column stabilization system, comprising at least two shank- or sleeve-shaped instruments.

BACKGROUND OF THE INVENTION

A medical instrumentarium of the kind described at the outset for implanting a spinal column stabilization system is known from DE 10 2013 108 362 A1, for example. The known instrumentarium comprises multiple sleeves that are coupleable to heads of bone screws thereby configured in particular as polyaxial screws. The bone screws are first anchored in pedicles of vertebrae of the spinal column to be stabilized and are therefore also referred to as pedicle screws. With a further instrument, connecting rods may be inserted in a simple manner into corresponding receivers on the heads of the pedicle screws. Spacings of the vertebrae from each other may be adjusted using known distractors by displacing the shank- or sleeve-shaped instruments in particular in parallel to each other and/or by pivoting them relative to each other. Such a procedure is described in particular in DE 10 2012 107 056 A1.

Known instrumentaria possess a high complexity and are time-consuming to operate. Further, certain damages to the spinal column of a patient require not only a certain spacing of the adjacent vertebrae from each other, but also a certain alignment and orientation, respectively, relative to each other. In order to achieve this, it is known to align bone screws and their heads, respectively, which are anchored in adjacent vertebrae, in a desired manner in order to restore an original position of adjacent vertebrae or to perform a correction of a malpostion. Performing such an angle adjustment using known instrumentaria is only very laboriously possible, because one must, for example, approach a desired correction angle, in particular a lordosis angle, step by step. In the known procedure, a correction adjustment performed by the surgeon alternates with a check by means of X-ray on the angle adjusted by him or her until the desired angle is achieved.

SUMMARY OF THE INVENTION

In a first aspect of the invention, a medical instrument for temporarily coupling to at least two shank- or sleeve-shaped instruments, comprises a first coupling device for temporarily coupling to a first shank- or sleeve-shaped instrument and a second coupling device for coupling to a second shank- or sleeve-shaped instrument. The first coupling device and the second coupling device are arranged or formed so as to be pivotable relative to each other. The medical instrument comprises a main body on which the first coupling device is guided and held so as to be pivotable about a point of rotation that in particular is spatially remote from the main body. The medical instrument comprises a first guide device for guiding a movement of the first coupling device along a circular path. The first guide device is arranged or formed at least partially on the main body. The first guide device comprises two or more circular arc shaped guide slots.

In a second aspect of the invention, a medical instrumentarium for implanting a spinal column stabilization system, comprises at least two shank- or sleeve-shaped instruments. The instrumentarium further comprises a medical instrument for temporarily coupling the at least two shank- or sleeve-shaped instruments. The medical instrument comprises a first coupling device for temporarily coupling to a first shank- or sleeve-shaped instrument and a second coupling device for coupling to a second shank- or sleeve-shaped instrument. The first coupling device and the second coupling device are arranged or formed so as to be pivotable relative to each other. The medical instrument comprises a main body on which the first coupling device is guided and held so as to be pivotable about a point of rotation that in particular is spatially remote from the main body. The medical instrument comprises a first guide device for guiding a movement of the first coupling device along a circular path. The first guide device is arranged or formed at least partially on the main body. The the first guide device comprises two or more circular arc shaped guide slots.

BRIEF DESCRIPTION OF THE DRAWING FIGURES

Figure 2:
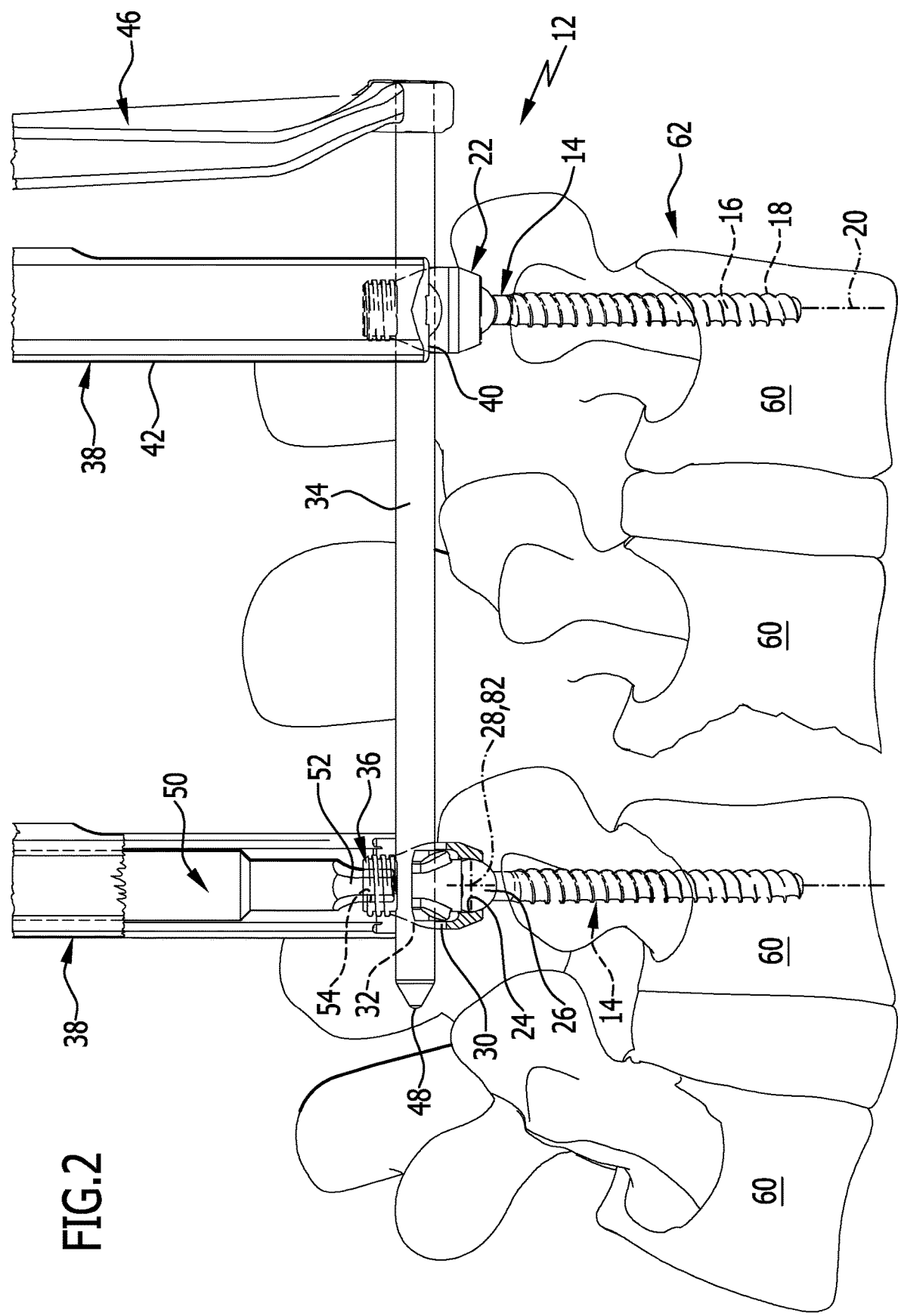
Figure 3:
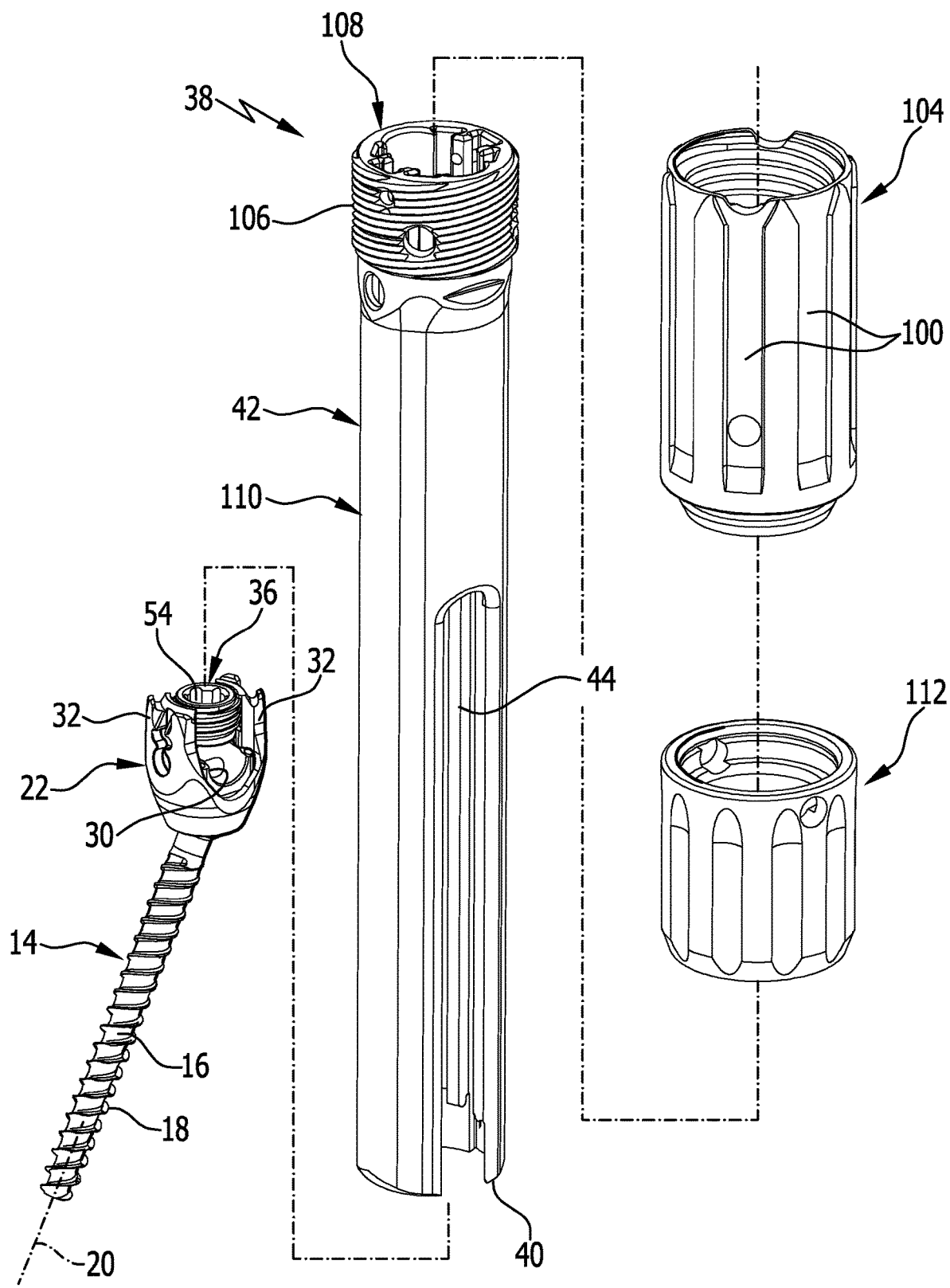
Figure 4:
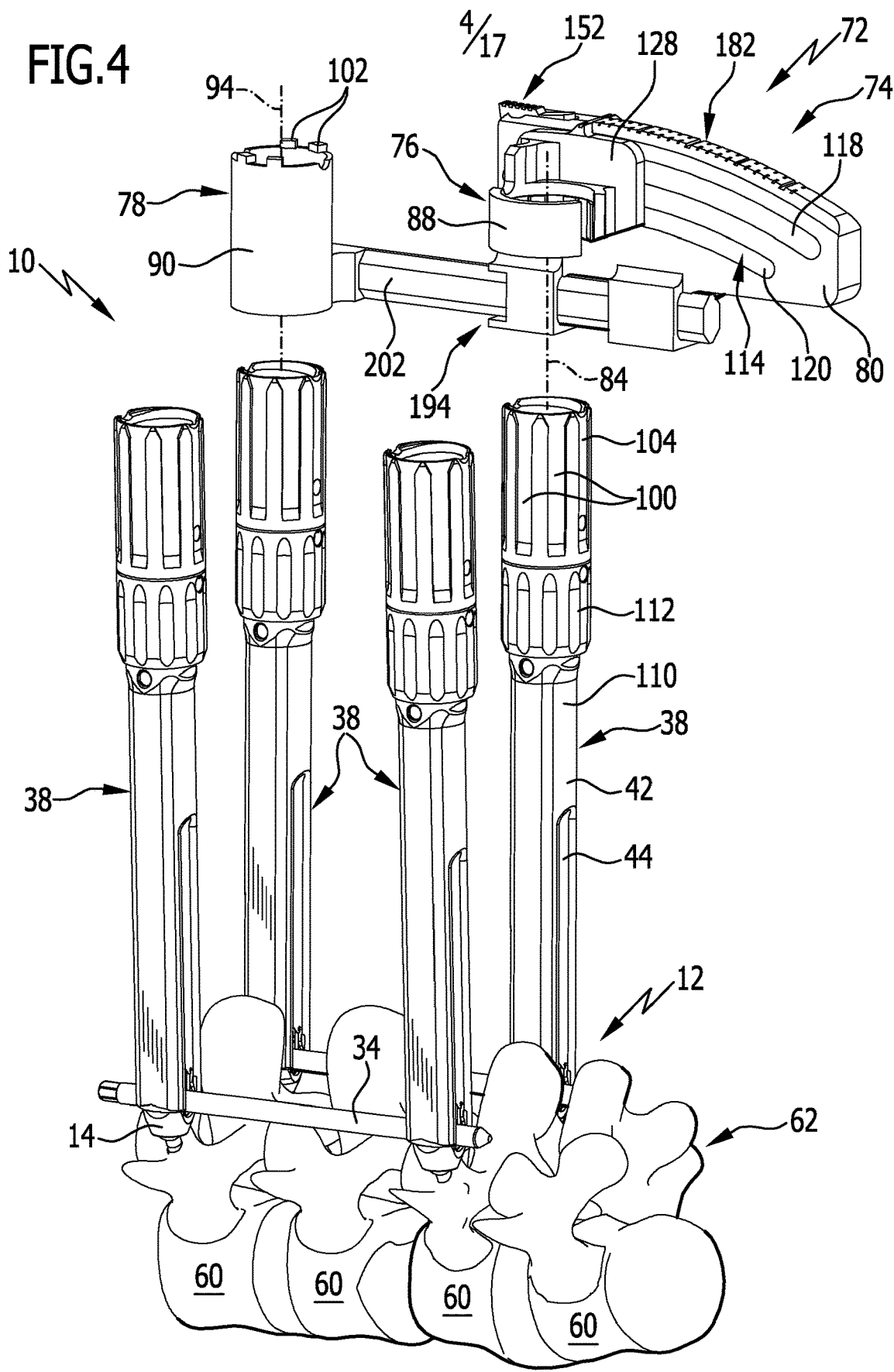
Figure 5:
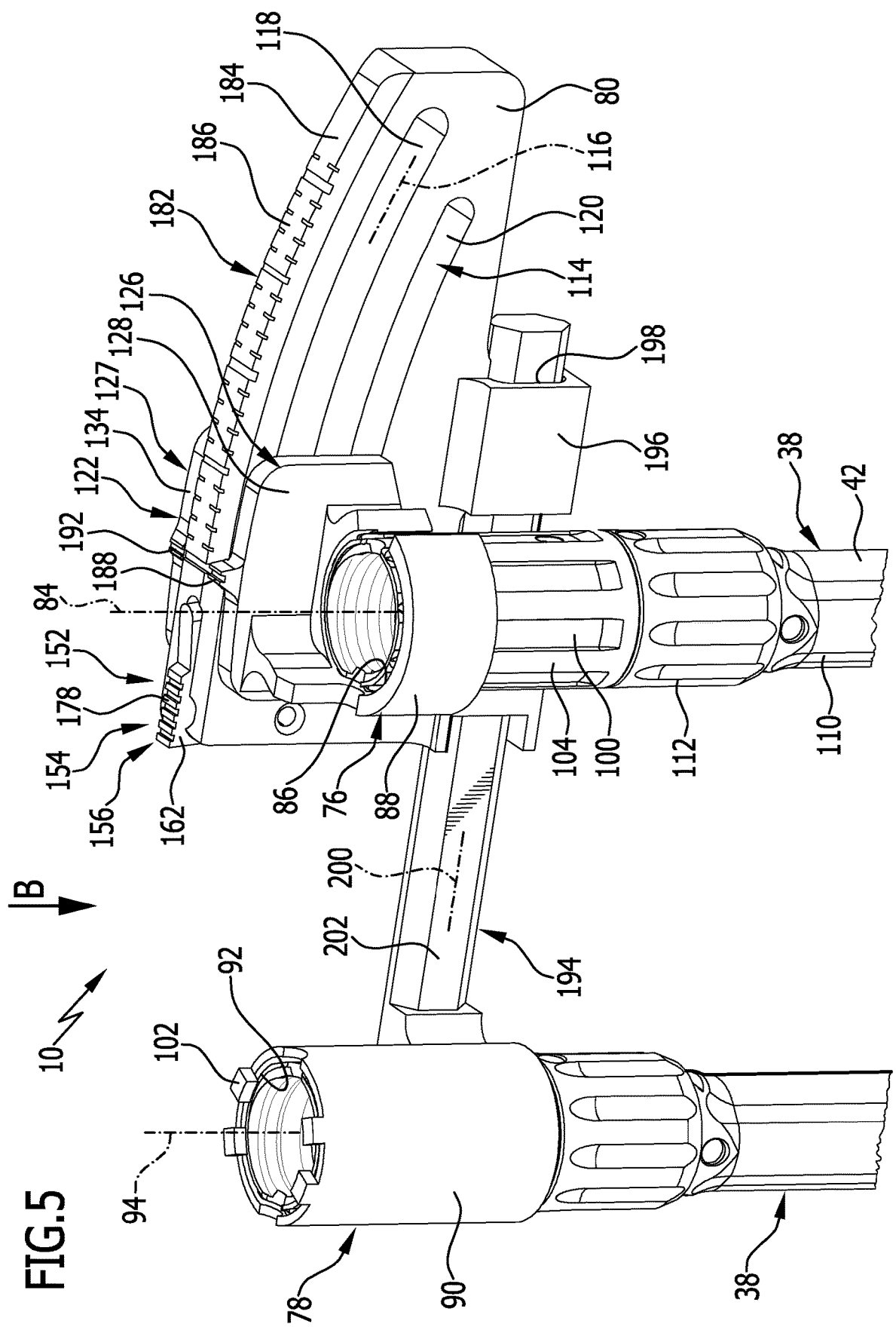
Figure 6:
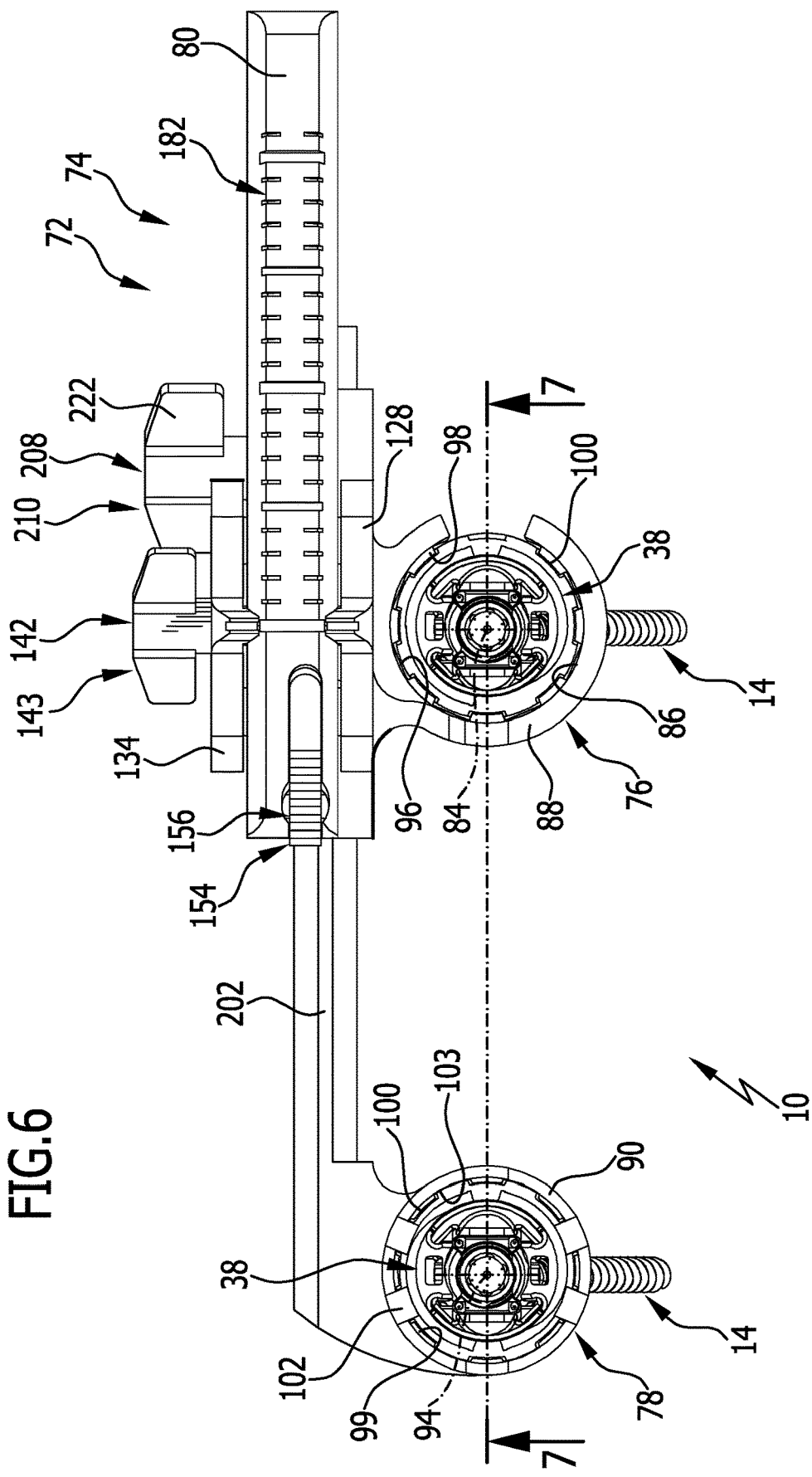
Figure 7:
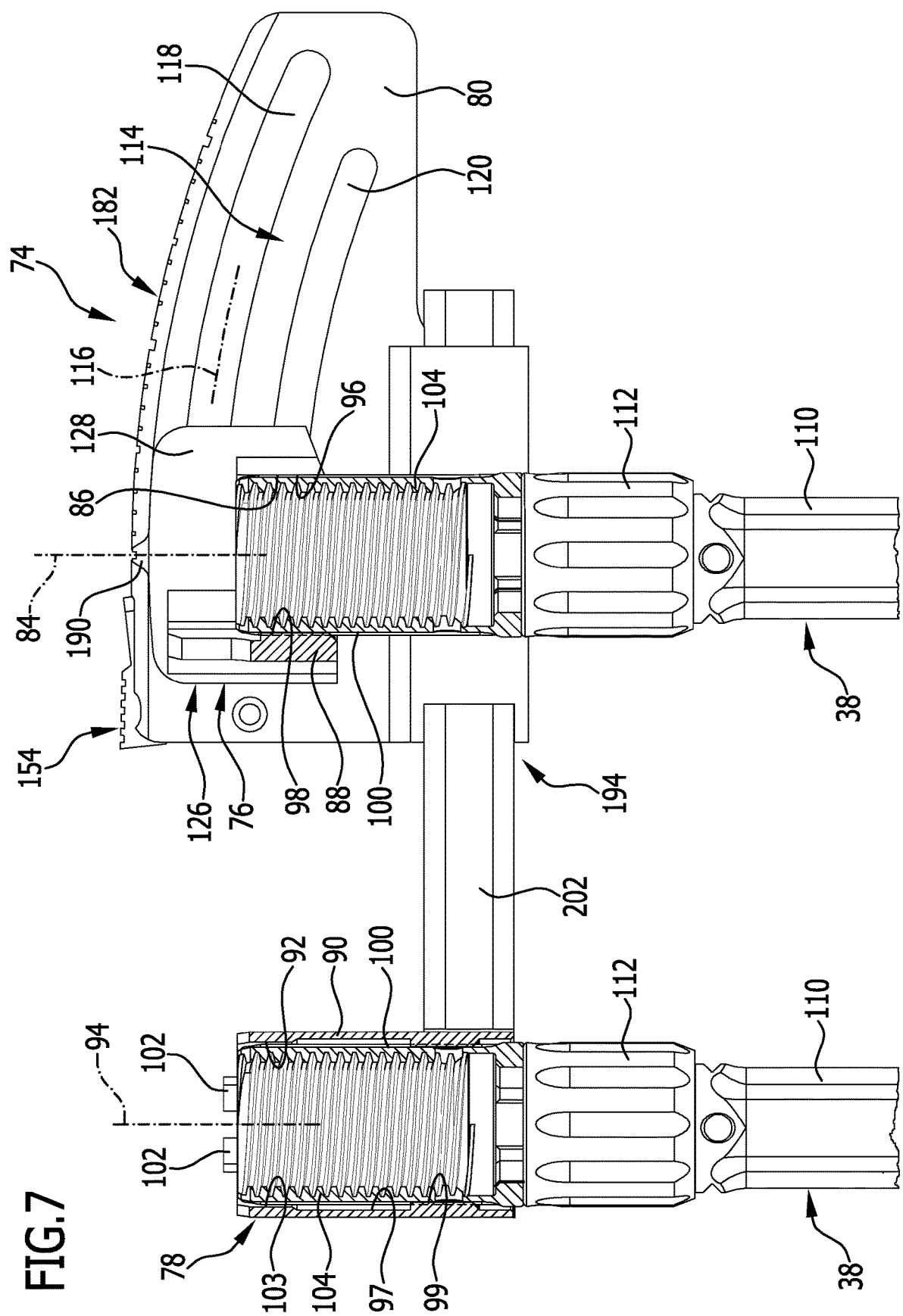
Figure 8:
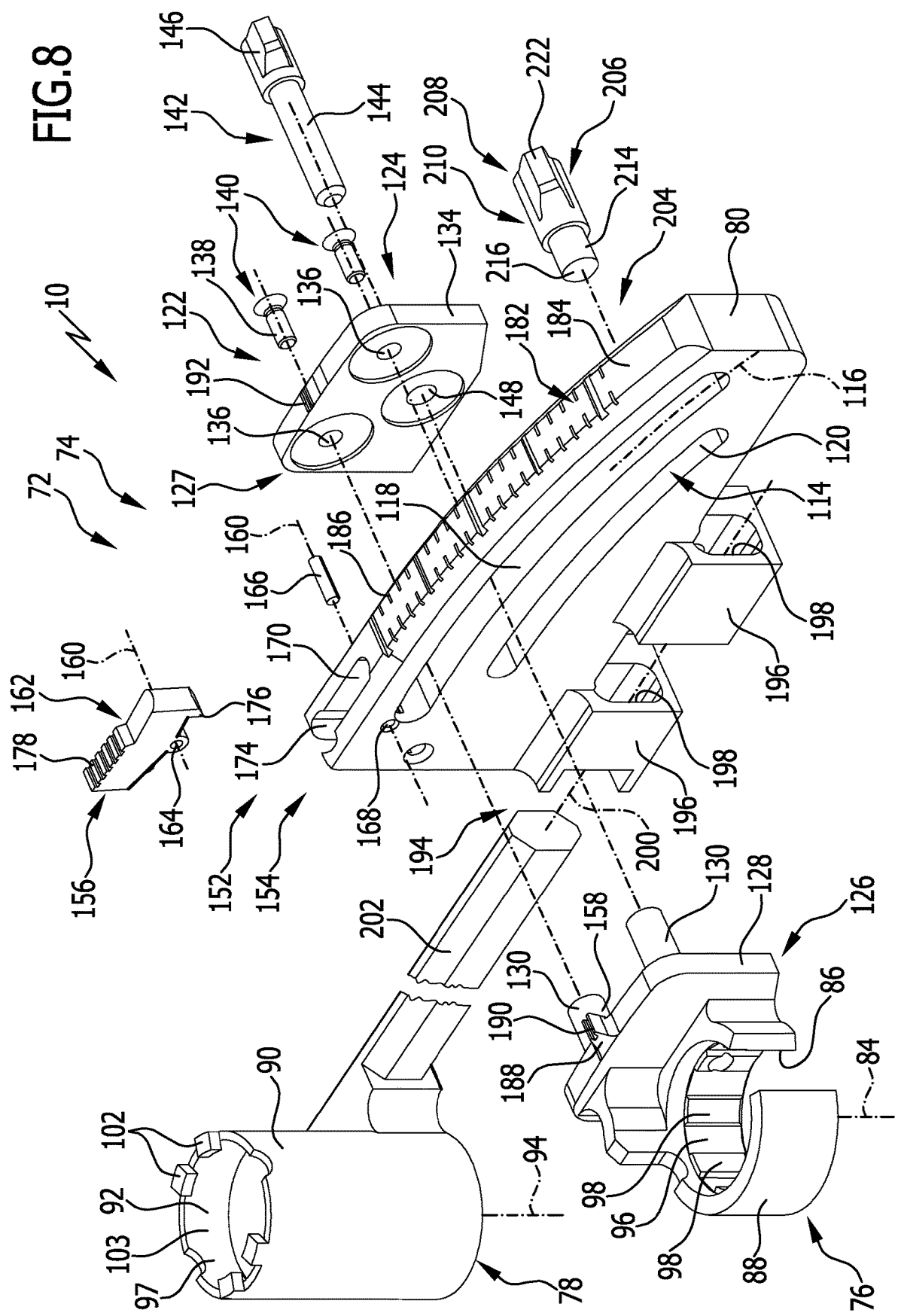
Figure 9:
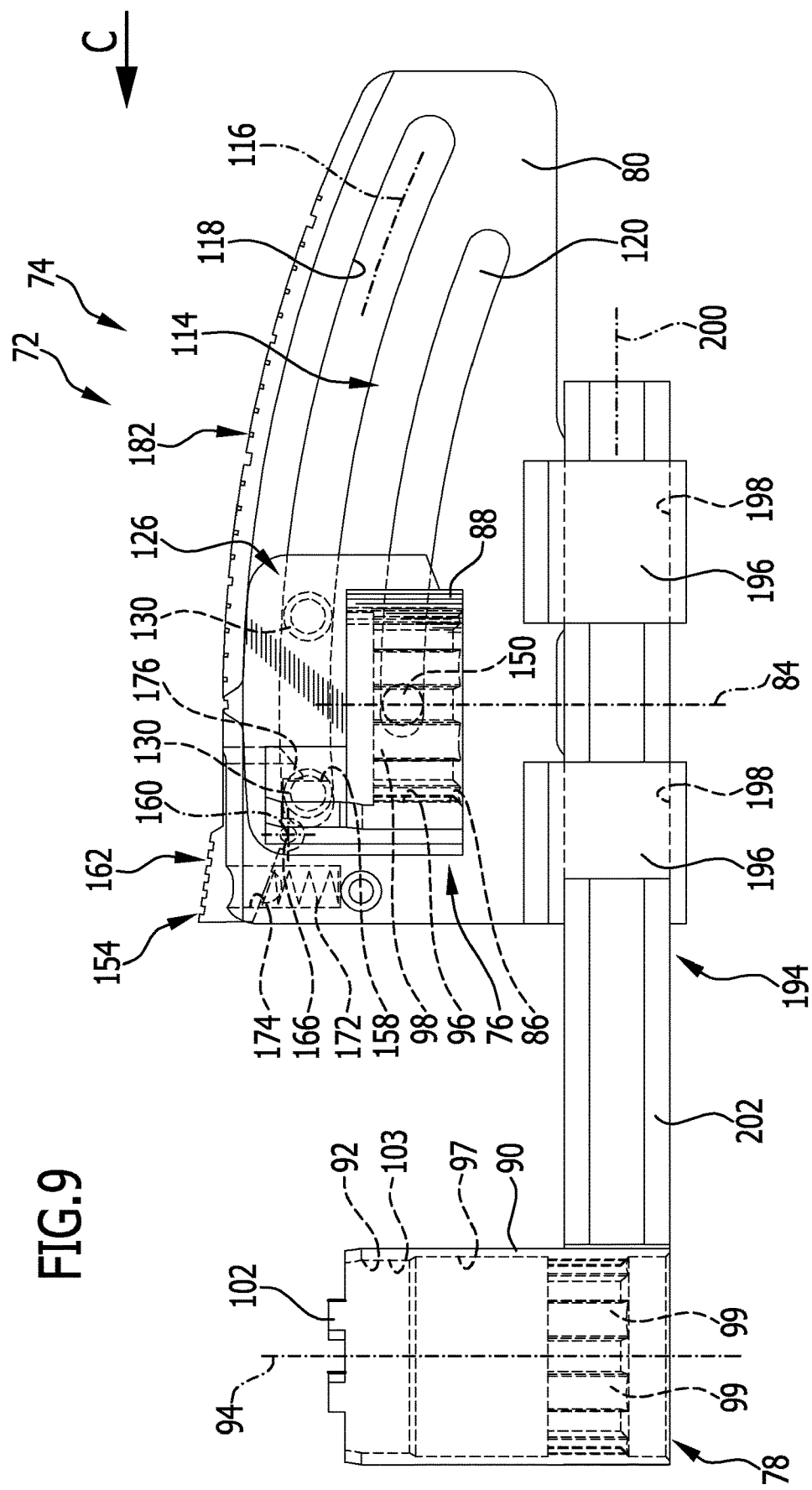
Figure 10:
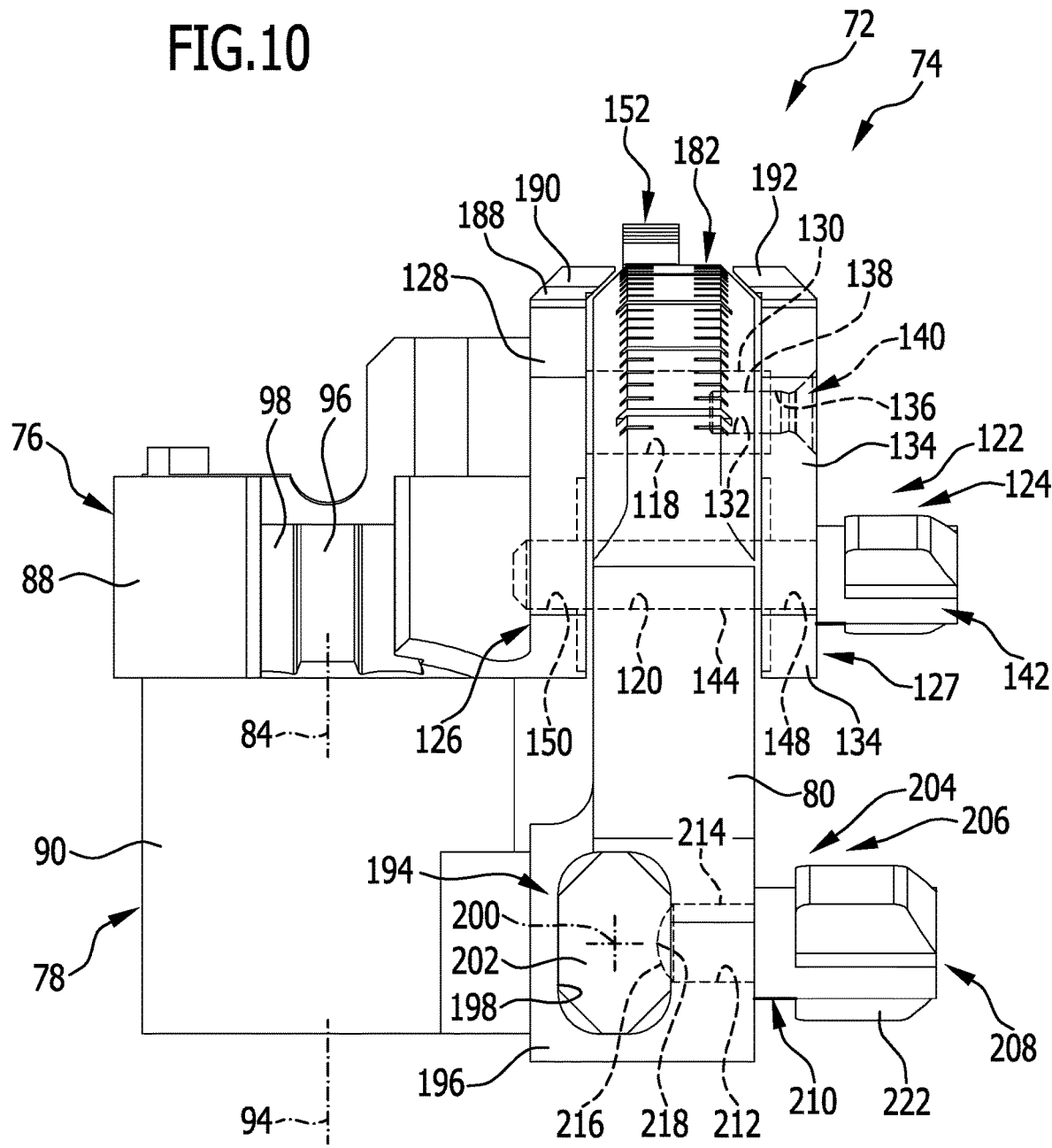
Figure 11:
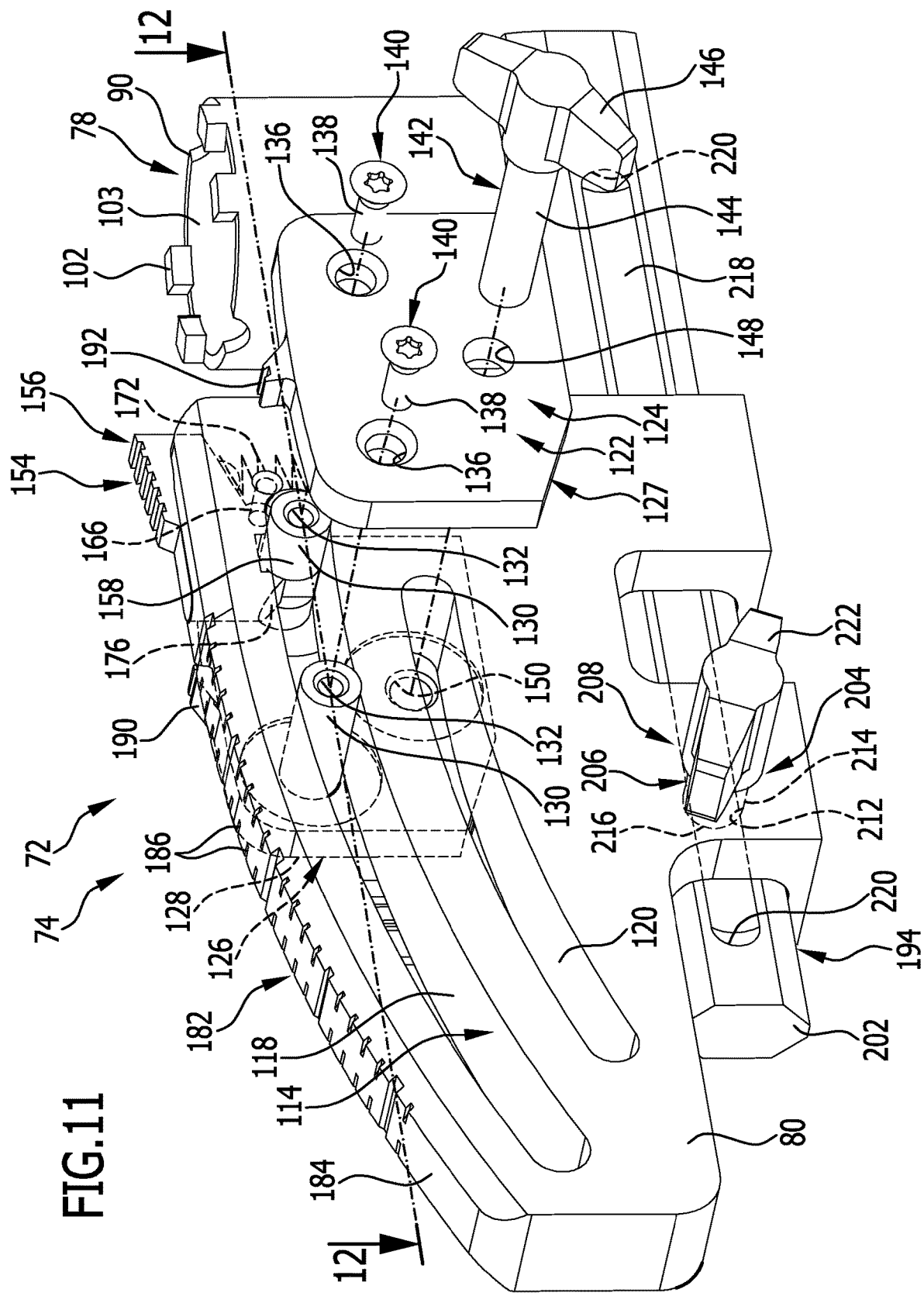
Figure 12:
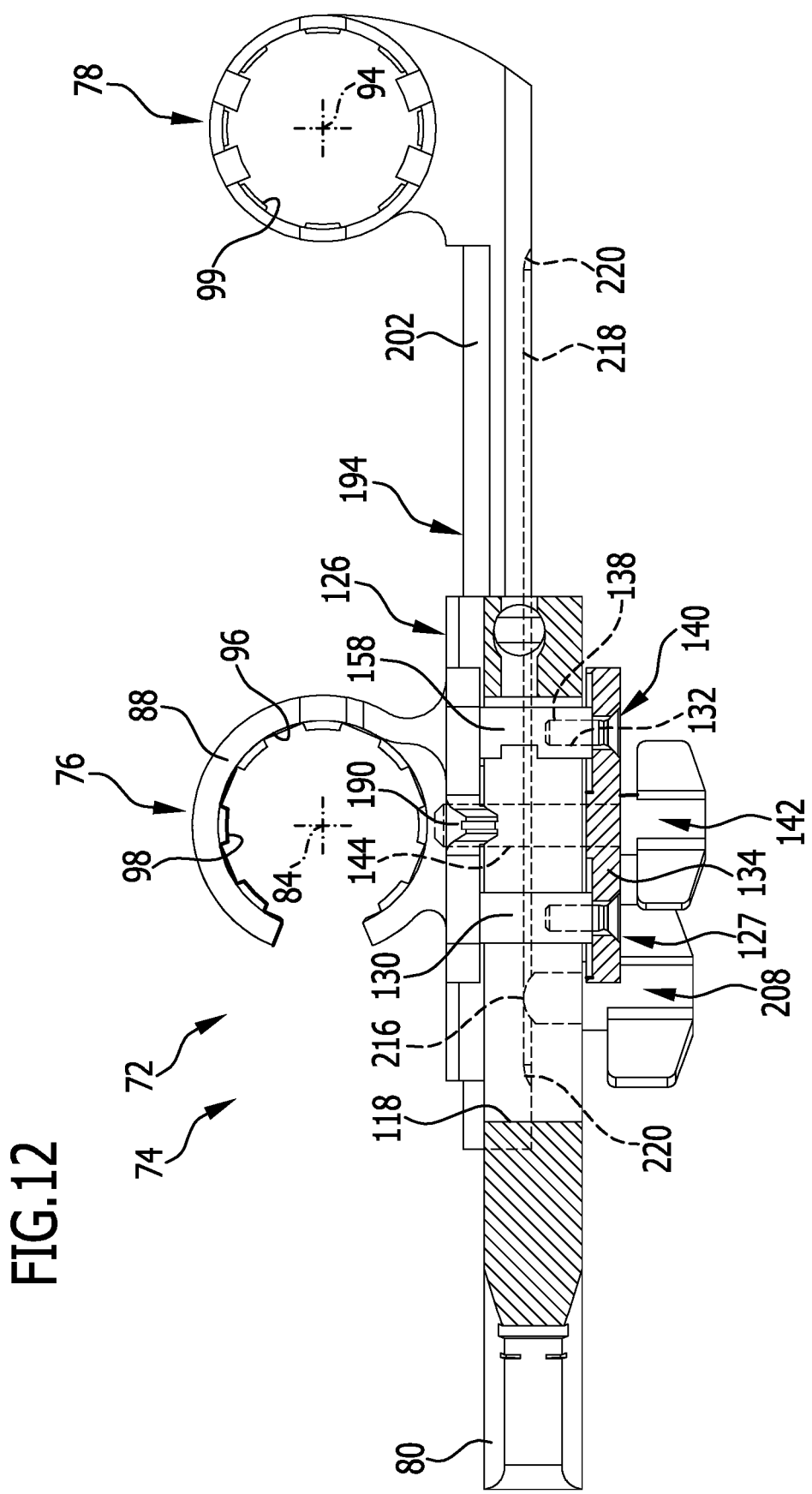
Figure 13:
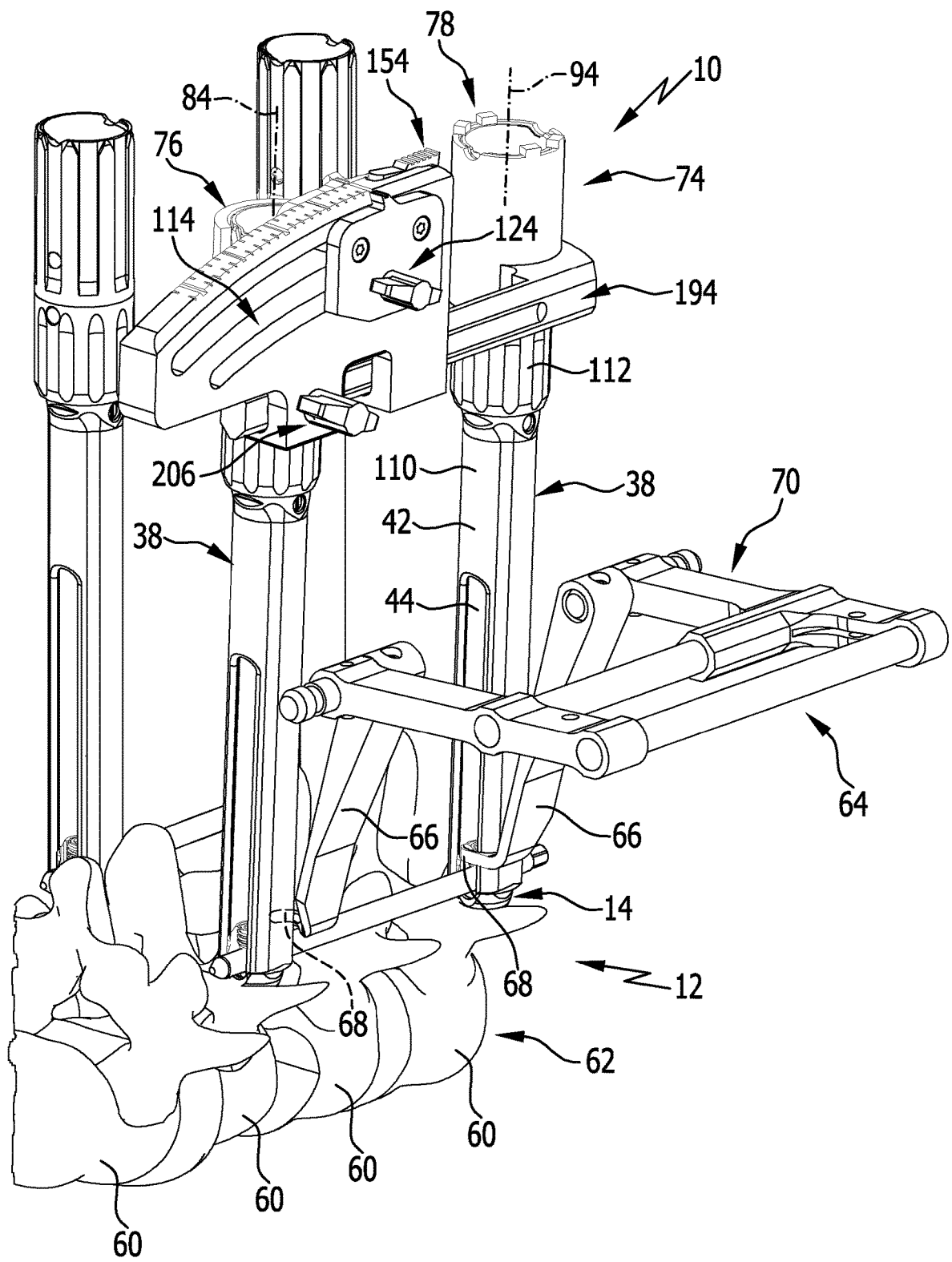
Figure 14:
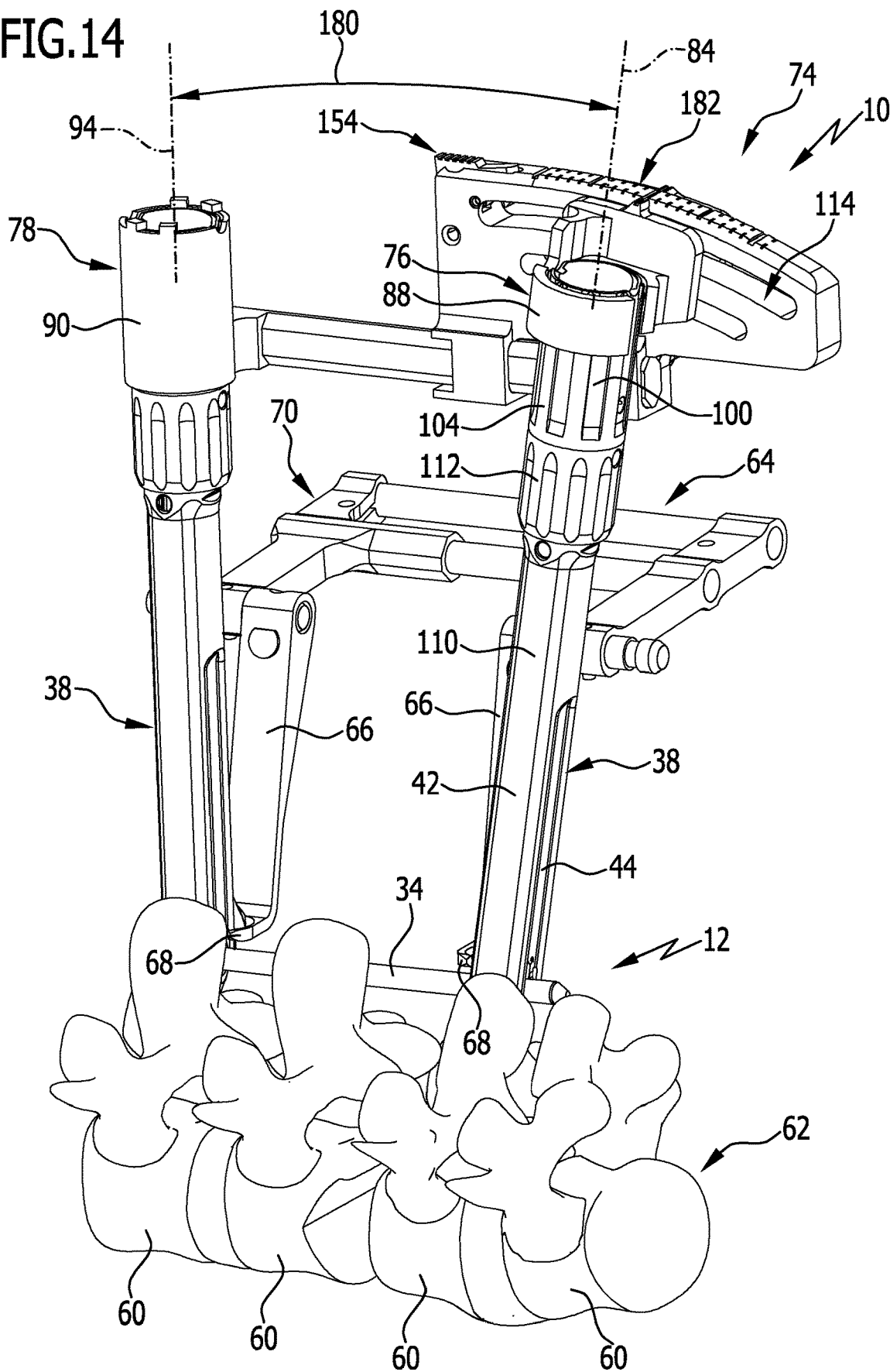
Figure 15:
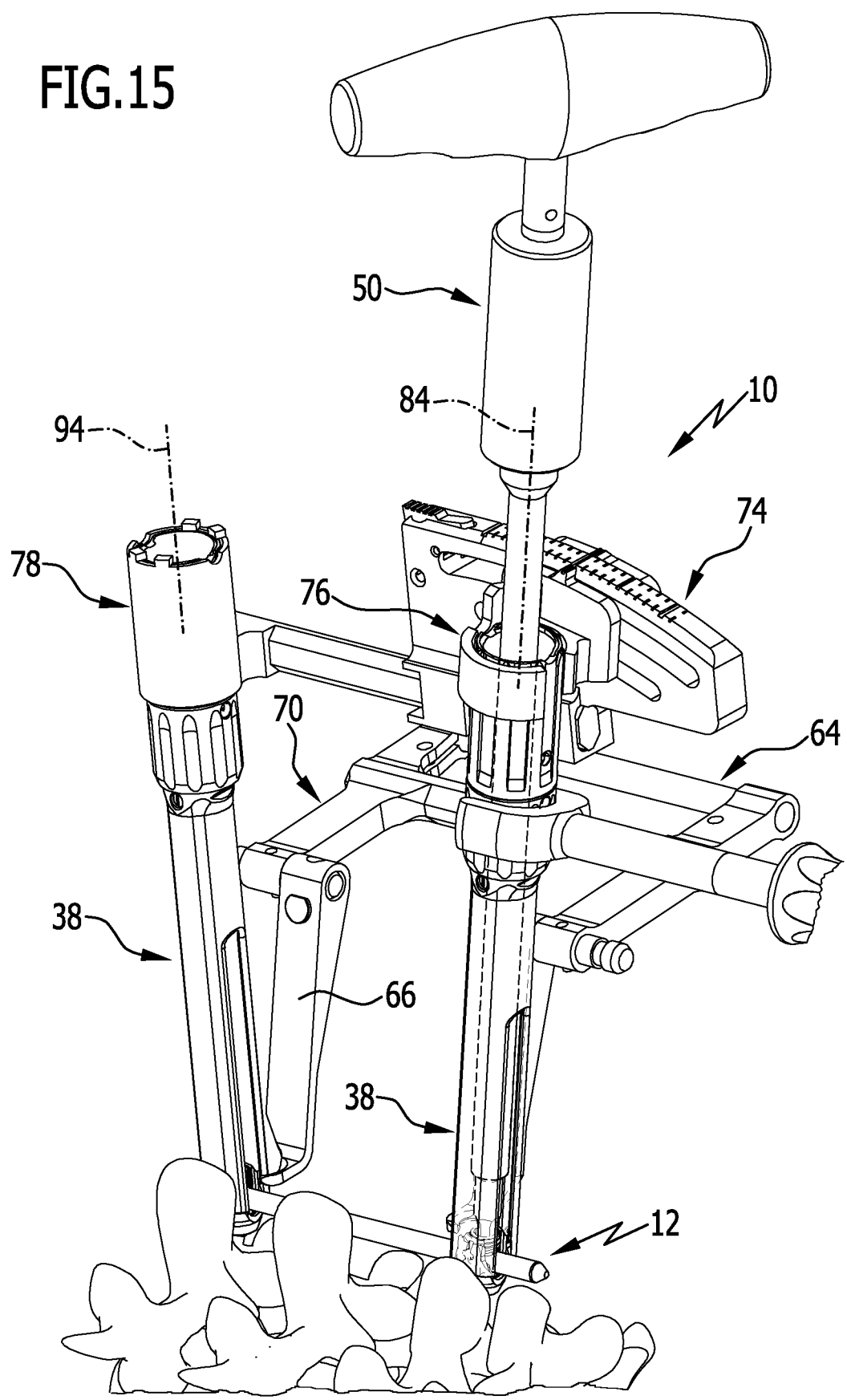
Figure 16:
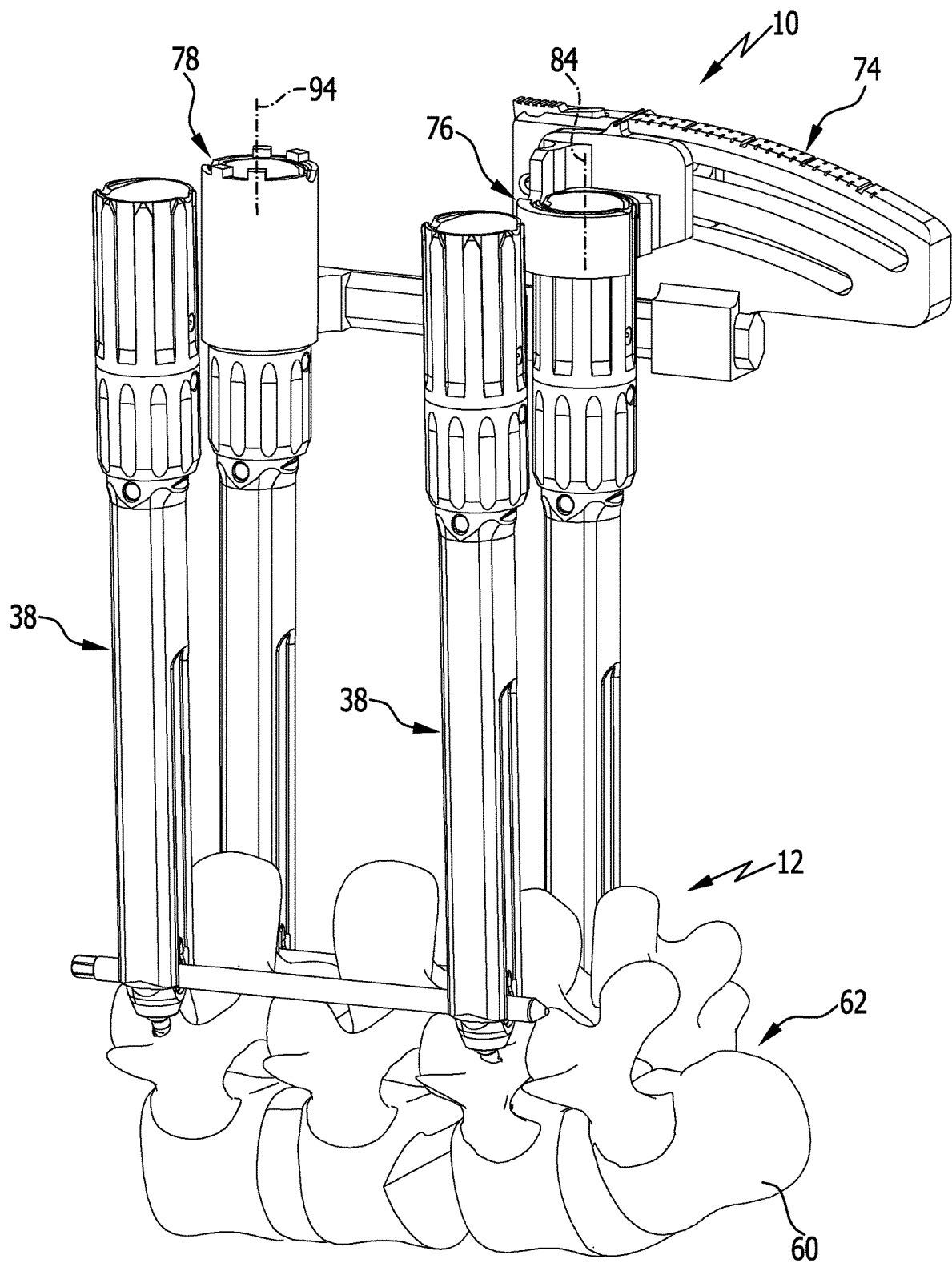
Figure 17:
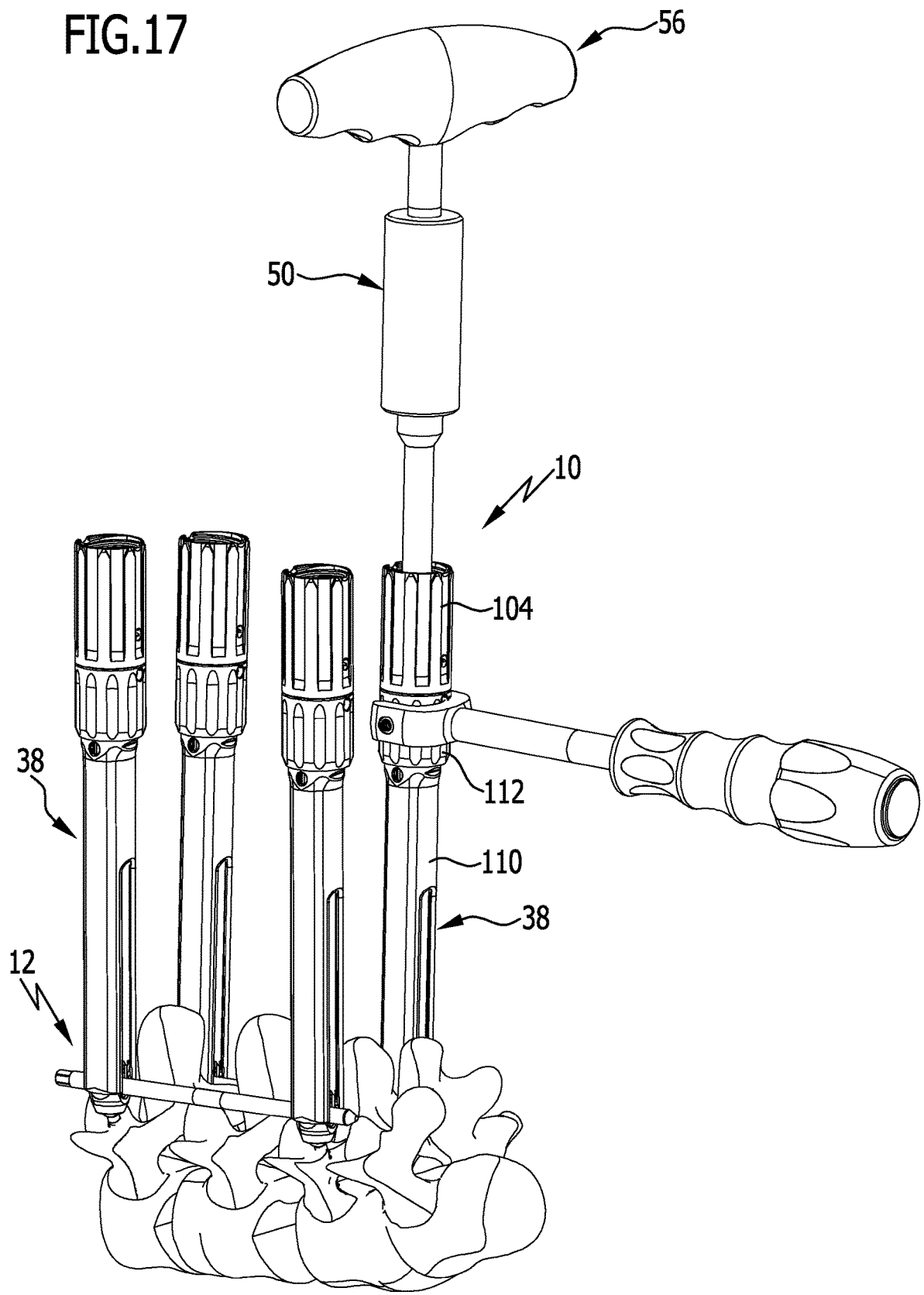

The foregoing summary and the following description may be better understood in conjunction with the drawing figures, of which:

FIG. 1: shows an exemplary perspective depiction of a part of a medical instrumentarium for implanting a spinal column stabilization system using a connecting rod in receivers on heads of two polyaxial screws;

FIG. 2: shows a partially broken view in the direction of the arrow A in FIG. 1;

FIG. 3: shows an exploded depiction of a shank- or sleeve-shaped instrument which is temporarily coupleable to a head of a polyaxial screw;

FIG. 4: shows a perspective total view of the instrumentarium having a medical instrument for temporarily coupling to two of a total of four shank- or sleeve-shaped instruments;

FIG. 5: shows a perspective view of the medical instrument coupled to two shank- or sleeve-shaped medical instruments;

FIG. 6: shows a view of the arrangement from FIG. 5 in the direction of the arrow B;

FIG. 7: shows a sectional view along line 7-7 in FIG. 6;

FIG. 8: shows an exploded depiction of the medical instrument for temporarily coupling to two shank- or sleeve-shaped instruments;

FIG. 9: shows a partially broken side view of the arrangement from FIG. 8;

FIG. 10: shows a view of the arrangement from FIG. 9 in the direction of the arrow C;

FIG. 11: shows a perspective, partial exploded view of the arrangement from FIG. 8;

FIG. 12: shows a sectional view along line 12-12 in FIG. 11;

FIG. 13: shows a perspective total view of a medical instrumentarium having a medical instrument for temporarily coupling to two shank- or sleeve-shaped instruments and a distractor;

FIG. 14: shows a partial view of the arrangement from FIG. 14 substantially from the opposite side;

FIG. 15: shows an arrangement similar to FIG. 14 upon fixing the connecting rod to a pedicle screw at a preset angle of the first and second coupling device of the medical instrument relative to each other;

FIG. 16: shows a perspective total view similar to FIG. 13, but without a distractor; and FIG. 17: shows a view similar to FIG. 16 upon fixing a further connecting rod to a pedicle screw.

DETAILED DESCRIPTION

Although the invention is illustrated and described herein with reference to specific embodiments, the invention is not intended to be limited to the details shown. Rather, various modifications may be made in the details within the scope and range of equivalents of the claims and without departing from the invention.

The present invention relates to a medical instrument for temporarily coupling to at least two shank- or sleeve-shaped instruments, comprising a first coupling device for temporarily coupling to a first shank- or sleeve-shaped instrument and a second coupling device for coupling to a second shank- or sleeve-shaped instrument, wherein the first coupling device and the second coupling device are arranged or formed so as to be pivotable relative to each other, which medical instrument comprises a main body on which the first coupling device is guided and held so as to be pivotable about a point of rotation that in particular is spatially remote from the main body, which medical instrument comprises a first guide device for guiding a movement of the first coupling device along a circular path, wherein the first guide device is arranged or formed at least partially on the main body, wherein the first guide device comprises two or more circular arc shaped guide slots.

The further development proposed in accordance with the invention makes it possible to couple two shank- or sleeve-shaped instruments to the medical instrument, and to correspondingly pivot the shank- or sleeve-shaped instruments relative to each other in a defined manner by way of relative pivoting of the first coupling device and the second coupling device, and to adjust in this manner a desired angle between these and, in particular, adjacent vertebrae. By pivoting the shank- or sleeve-shaped instruments relative to each other, the heads of the screws of the spinal column stabilization system and also, as the case may be, the shanks of the bone screws are aligned in a corresponding manner. Unlike in the previous procedure, a correction adjustment must not be performed and alternatingly be checked by means of an X-ray image, but rather, for example, a necessary correction angle determined using X-ray images captured before the surgical operation may be directly carried over using the proposed medical instrument by pivoting the first coupling device and the second coupling device relative to each other through the correction angle. Multiple X-ray checks and lengthy correction adjustments and readjustments are no longer necessary with the proposed instrument.

It is favorable if the first coupling device and the second coupling device are arranged or formed so as to be displaceable relative to each other. Optionally to the relative pivotability of the first coupling device and the second coupling device relative to each other, the relative displaceability also enables specifically changing a spacing of the two shank- or sleeve-shaped instruments and thus also a spacing of the bone screws and their heads, respectively, which are coupled to the shank- or sleeve-shaped instruments.

In accordance with another preferred embodiment, provision may be made for the instrument to comprise a main body on which the first coupling device is guided and held so as to be pivotable about a point of rotation. In particular, the point of rotation may be concerning a point of rotation that is spatially remote from the main body. For example, the point of rotation may be defined by a midpoint of a ball joint that is formed between a head and a shank of the screw, in the case of a polyaxial screw. Angles and/or spacings between bone screws may be specifically adjusted in this way.

It is favorable if the second coupling device is displaceably guided and held on the main body. In particular a spacing between the first and the second coupling device may thus be specifically changed by displacing the second coupling device relative to the main body. In particular, a displacement of the second coupling device on the main body along a straight and/or curved path may take place.

It is advantageous if the first coupling device and/or the second coupling device are configured in the form of a receiver for a shank- or sleeve-shaped instrument, which defines a coupling device longitudinal axis. This design enables in particular coupling the medical instrument to one or two shank- or sleeve-shaped instruments in a simple manner.

The medical instrument may be constructed in a particularly simple manner if the receivers are configured in the form of retaining rings or retaining arcs. For example, the retaining rings may be closed in themselves and have an adequate extension in parallel to the coupling device longitudinal axis of the respective coupling device, in order to prevent as much as possible a tilting of the shank- or sleeve-shaped instrument relative to the coupling device. A retaining arc may for example be formed to be C-shaped and preferably comprises an angle range of more than 180°, in order to securely hold the shank- or sleeve-shaped instrument on one of the two coupling devices as captively as possible.

It is favorable if at least one protruding coupling projection is arranged or formed at the receivers for coupling to a shank- or sleeve-shaped instrument in a non-positive- and/or positive-locking manner. The at least one coupling projection enables bringing the shank- or sleeve-shaped instrument into engagement with said coupling device in a specific manner, for example secured against a rotation relative to the coupling device.

The at least one coupling projection is preferably formed projecting from an inner wall face toward the coupling device longitudinal axis. For example, the at least one coupling projection—two, three, or more coupling projections may also be provided—may engage in corresponding recesses on the shank- or sleeve-shaped instrument, in order to prevent a rotation thereof relative to the coupling device. In addition, a guidance of the shank- or sleeve-shaped instrument on the coupling device may thus be achieved. Receivers that correspond to the at least one coupling projection may in particular be open pointing radially away from the coupling device longitudinal axis.

In accordance with another preferred embodiment, provision may be made for the medical instrument to comprise a first guide device for guiding a movement of the first coupling device along a circular path. Such a guide device enables in particular moving the first and the second coupling device relative to each other such that they may perform a pivotal movement relative to each other about a midpoint defined by the circular path. In particular, a curvature of the circular path may be adapted to a length of the shank- or sleeve-shaped instruments to be coupled to the coupling devices, so that a midpoint of the circular path coincides with a point of rotation of a polyaxial screw, for example. In the case of a spacing of two polyaxial screws relative to each other which remains constant, their orientation may be altered in a simple manner. If, for example, shank- or sleeve-shaped instruments in two different lengths are used, a curvature of the circular path may be provided such that it corresponds to a mean value of the two different lengths.

The medical instrument may be constructed in a particularly simple manner if the first guide device is arranged or formed at least partially on the main body and comprises at least one circular arc shaped guide slot. For example, the main body may be configured in the form of a plate or comprise a plate in which a circular arc shaped guide slot is formed. Two or more circular arc shaped guide slots may also be formed. These are preferably formed concentrically to each other on the main body.

The medical instrument preferably comprises two circular arc shaped slots arranged concentrically to each other. These enable in particular moving the first coupling device with a defined alignment relative to the main body and thus to the second coupling device, in particular pivoting them about a common point of rotation.

It is particularly advantageous if the medical instrument comprises a fixing device for fixing the first coupling device in a first orientation on the main body. A relative angle between the first and second coupling device may thus not only be specifically adjusted, but also fixed in the first orientation.

It is advantageous if the first fixing device is configured in the form of a clamping device. A clamping device may be constructed in various ways and enables a fast and simple release and fixing thereof.

It is favorable if the clamping device comprises first and second clamping elements that are coupled to each other by the connecting members penetrating the at least one guide slot and that comprise a first clamping member for moving the first and second clamping elements toward each other. This configuration enables in particular guiding the first coupling device in a defined manner on the main body, on the one hand, and fixing the first and second clamping elements on the main body in the first orientation by way of the first clamping member by moving them toward each other.

A particularly simple handling of the instrument is enabled if the first clamping member is configured in the form of a clamping screw which at least partially penetrates the at least one guide slot and is able to be brought from an adjusting position into a clamping position and vice versa. In order to fix the first coupling device in the orientation on the main body, the clamping screw must merely be brought into the clamping position. In order to be able to move the first coupling device again, the clamping screw must merely be released again, i.e. transferred into the adjusting position, so that the first coupling device may be moved again relative to the main body and relative to the second coupling device.

A particular compact construction of the medical instrument may be achieved in particular by the first clamping element comprising or bearing the first receiver. In particular, the first clamping element may be integrally formed with the first receiver. A defined alignment of the receiver relative to the main body may thus already be predetermined during production.

In accordance with another preferred embodiment, provision may be made for the medical instrument to comprise a locking device for locking the first coupling device on the main body in a normal position, in which the coupling device longitudinal axes of the at least two coupling devices are aligned in parallel to each other. The locking device enables in particular bringing the instrument into a defined normal position in which the coupling device longitudinal axes in particular of the first and the second coupling device are aligned in parallel to each other. Starting from said normal position, after releasing the locking device, the instrument may, for example, be used to adjust a desired relative angle between the first and the second coupling device.

It is advantageous if the locking device comprises a latching connecting device having a moveable first latching member and a second latching member, and if the first and the second latching member are engaged in a non-positive- and/or positive-locking manner in the normal position and are disengaged in a release position. In the release position, the first coupling device may be moved relative to the main body, for example. The described latching connecting device may be achieved in particular in a simple manner and with a minimal number of moving parts. In particular, it may also be optimized for an intraoperative handling.

The latching connecting device may be constructed in a simple manner if the first latching member is configured in the form of a latching lever that is displaceably and/or pivotally mounted on the main body and which has a projection or a recess which is engaged in the normal position with a corresponding recess or a corresponding projection on the first coupling device. To release the latching connecting device, the first latching member must merely be displaced and/or pivoted in such a way that it becomes disengaged with the second latching member, so that the latching connecting device assumes the described release position.

The handling of the instrument may be further improved if the first latching member is mounted so as to be pivotable about a pivotal axis which runs transversely, in particular perpendicularly, to the coupling device longitudinal axis of the first and/or second coupling device. In this way, the first coupling device may be held on the main body in the normal position, in particular with minimal forces. The pivotal axis may further run parallel to an axis that is defined by the first guide device, about which the first and the second coupling device may be pivoted relative to each other.

For a particularly simple handling of the medical instrument, it is favorable if it comprises a display device for displaying an angle between the coupling device longitudinal axes of the at least two coupling devices.

The display device may be constructed in a particularly simply manner if it comprises angle markings on the main body, and a display member, arranged or formed on the first coupling device, which points to the angle markings. Such a display device may in particular also be cleaned well intraoperatively, for example by rinsing with water or an isotonic saline solution.

In order to construct the medical instrument particularly compactly, it is favorable if the display member is arranged or formed on the first and/or second clamping element.

In accordance with another preferred embodiment, provision may be made for the medical instrument to comprise a second guide device for guiding a movement of the second coupling device along a linear path. The second guide device enables in particular moving the first and the second coupling device relative to each other along a linear path, i.e. specifically changing a spacing between them, for example.

Furthermore, the instrument may be particularly compactly constructed if the second guide device is formed on the main body and comprises at least one guide receiver. In particular, two guide receivers may also be provided, which allow a particularly stable and true-to-path guidance of the second coupling device on the main body.

It is advantageous if the second coupling device comprises a rod- or shank-shaped guide member which is guided and held in or at the at least one guide receiver. For example, the guide receiver may be configured in the form of a ring, into which the rod- or shank-shaped guide member is inserted and is displaceably held therein. Two guide receivers may also be provided, which enable an improved guidance of the rod- or shank-shaped guide member.

It may be further favorable if the medical instrument comprises a second fixing device for fixing the second coupling device in a second orientation on the main body. The second fixing device makes it possible in particular, similar to the first fixing device, to now fix the second coupling device relative to the main body in a defined position, namely in the second orientation. As a result, a desired spacing between the first and the second coupling device may in particular not only be adjusted, but also temporarily fixed.

The second fixing device may be constructed in a particularly simple manner if it is configured in the form of a clamping device. In particular, the second coupling device may thus be held in a clamping manner on the main body in the second orientation.

It is advantageous if the second clamping device comprises at least one second clamping member for fixing the guide member on the main body in a clamping manner.

It is favorable if the second clamping member is configured in the form of a clamping screw which penetrates the at least one guide receiver and, in the second orientation, presses against the guide member with a free shank end of a clamping screw shank. In particular, on the guide member may be formed a groove-shaped guide recess, into which the free shank end of the clamping screw shank presses in the second orientation. In particular, a twisting of the guide member in the at least one guide receiver may be prevented by the guide recess. The guide member may optionally also have a non-round cross-section, so that a twisting of the guide member about a longitudinal axis in a guide receiver, which has a corresponding internal cross-section that is matched to the cross-section of the guide member, may also be prevented.

In order to prevent an undesired detachment of the second coupling device from the main body, it is advantageous if the guide recess defines end stops for a displacement movement of the guide member relative to the main body. If, for example, the free shank end of the clamping screw shank protrudes into the groove-shaped guide recess, the guide member may thus be pushed back and forth only so far until the free shank end strikes against one of the end stops, for example stop faces which are formed on both sides of the guide recess and point toward each other.

The invention also relates to a medical instrumentarium for implanting a spinal column stabilization system, comprising at least two shank- or sleeve-shaped instruments, wherein the instrumentarium further comprises a medical instrument for temporarily coupling the at least two shank- or sleeve-shaped instruments, said medical instrument comprising a first coupling device for temporarily coupling to a first shank- or sleeve-shaped instrument and a second coupling device for coupling to a second shank- or sleeve-shaped instrument, wherein the first coupling device and the second coupling device are arranged or formed so as to be pivotable relative to each other, which medical instrument comprises a main body on which the first coupling device is guided and held so as to be pivotable about a point of rotation that in particular is spatially remote from the main body, which medical instrument comprises a first guide device for guiding a movement of the first coupling device along a circular path, wherein the first guide device is arranged or formed at least partially on the main body, wherein the first guide device comprises two or more circular arc shaped guide slots.

A medical instrumentarium constructed in this way enables in particular implanting a spinal column stabilization system in a simple manner, in particular anchoring bone screws, for example in the form of pedicle screws, in vertebral bodies in a desired manner with specified spacing and a relative alignment angle in vertebrae of the spinal column.

Depicted exemplarily in the FIGS. 1 to 17 is a medical instrumentarium 10 for implanting a spinal column stabilization system 12.

The spinal column stabilization system 12 comprises multiple bone screws 14 that may in particular be configured in the form of polyaxial screws having an elongated shank 16 which is provided with an external threading 18 and which defines a shank longitudinal axis 20, and having a head 22 which has a seating 24 for a spherical proximal end 26 of the shank 16, such that the head 22 is pivotable relative to the shank 16 about a midpoint 28 of the spherical end 26.

The head 22 has a substantially U-shaped rod receiver 30 that is formed between two wall sections 32 which are provided with internally threaded sections. A connecting rod 34 of the spinal column stabilization system 12 may be inserted into the rod receiver 30 and be fixed to a fixing screw 36 whose external threading corresponds to the internally threaded sections of the wall sections 32.

The bone screw 14 may in particular also be configured in such a way that not only the connecting rod 34 may be fixed to the head 22 using the fixing screw 36, but also that the head 22 is immovably fixable on the spherical end 26 of the shank 16.

The instrumentarium 10 further comprises multiple shank- or sleeve-shaped instruments 38 whose distal end 40 is configured to temporarily couple to the head 22 in a known manner. The instrument 38 may in particular comprise an outer sleeve 42 which, commencing from the end 40, has a slot 44 extending in parallel to a longitudinal axis of the outer sleeve 42. The slot 44 of the instrument 38 is aligned with the head 22 such that the connecting rod 34 held on an insertion instrument 46 is insertible into the rod receiver 30 from the side. An insertion opening for a free end 48 of the connecting rod 34 is in particular delimited by the wall sections 32, the seating 24, and the fixing screw 36.

A screwing-in element 50, which is guidable through the outer sleeve 42 to the head 22 with its distal end and which at its distal end has a tool element 52 which is formed correspondingly to a tool element receiver 54 of the fixing screw 36 pointing in proximal direction, serves for fixing the connecting rod 34 in the rod receiver 30. The tool element receiver 54 is depicted exemplarily in the Figures in the form of an internal multi-round. Alternatively, the tool element receivers of the bone screws 14 are also possible in the form of a polygonal socket or a slot.

For a simple handing, the screwing-in instrument 50 is equipped with a ratchet grip 56 on the proximal side, in order to allow a surgeon to tighten the fixing screw on the head 22 in a simple manner. In particular, the ratchet grip 56 may be equipped with a torque limiting device 58, in order to not exceed a predefined tightening torque of the fixing screw 36.

For the implantation of the spinal column stabilization system 12, first the necessary number of bone screws 14 is screwed into the vertebrae 60 of the spinal column 62 that are to be positioned relative to each other. For an optimal stabilization of the spinal column 62, bone screws 14 are screwed into the pedicle of the vertebrae 60, for example on both sides of the spinous processes of the vertebrae 60.

As already described, the heads 22 may first be pivoted relative to the shanks 16 of the bone screws 14 about the midpoint 28. The instruments 38 serve for a simple and, in particular, minimally invasive handling of the spinal column stabilization system 12 and of the instrumentarium 10. These are coupled to the heads 22 and thus form extensions thereof that protrude out of the body of the patient.

In order to be able to specifically adjust a spacing between the bone screws 14 of adjacent vertebrae 60, the instrumentarium 10 may in particular comprise a distractor 64 having two legs 66 running parallel to each other whose distal ends 68 are coupleable to the instruments 38 in the region of their distal ends 40. Proximal ends of the legs 66 are coupled by a distraction bracket 70, with which a spacing between the legs 66 is variable and fixable.

The instrumentarium 10 comprises a further instrument 72 in the form of an angle adjuster 74. The angle adjuster 74 is configured to temporarily couple to two instruments 38 and comprises a first coupling device 76 and a second coupling device 78. The coupling devices 76 and 78 are arranged and formed, respectively, on the instrument 72 so as to be pivotable relative to each other. Furthermore, the coupling devices 76 and 78 are arranged and formed, respectively, on the instrument 72 so as to also be displaceable relative to each other.

The angle adjuster 74 comprises a plate-shaped main body 80 on which the first coupling device 76 is guided and held so as to be pivotable about a point of rotation that is spatially remote from the main body 80 and which preferably corresponds with the midpoint 28 of the bone screw 14, with which the instrument 38 coupled to the first coupling device 76 is temporarily connected. In particular, a pivotal axis, which is defined by the angle adjuster 74 and about which the coupling devices 76 and 78 are pivotable relative to each other, may comprise the point of rotation 82, and the point of rotation 82 lies on the pivotal axis, respectively.

The second coupling device 78 is displaceably guided and held on the main body 80.

The first coupling device 76 comprises a receiver 86 for the instrument 38, which defines a first coupling device longitudinal axis 84. The receiver 86 is configured in the form of a sleeve-shaped retaining arc 88, which is substantially C-shaped and encloses an angle range of more than 270°.

The second coupling device 78 comprises a sleeve-shaped retaining ring 90, which is closed in itself and which forms a receiver 92 for a proximal end of an instrument 38 and defines a second coupling device longitudinal axis 94.

Strip-shaped coupling projections 98 which run parallel and which are formed correspondingly to coupling recesses 100 on the instrument 38, protrude from an inner wall 96 of the retaining arc 88 in parallel to the first coupling device longitudinal axis 84 and point toward it. The coupling recesses 100 are configured in the form of longitudinal grooves which run parallel to the first coupling device 76 and which are open in radial direction pointing away from the first coupling device longitudinal axis 84.

On the retaining ring 90 at an proximal end are arranged multiple coupling projections 102 which project in the direction toward the second coupling device longitudinal axis 94 and which may likewise engage in coupling recesses 100 on the instrument 38. In addition, there are also formed strip-shaped coupling projections 99 that run parallel and which are formed correspondingly to coupling recesses 100 on the instrument 38, protruding from an inner wall 97 of the retaining ring 90 in parallel to the second coupling device longitudinal axis 44 and pointing toward it.

The coupling recesses 100 are formed on extension sleeves 104 that are temporarily coupleable to proximal ends 108 of the coupling sleeves 112 comprised by the instrument 38, which ends 108 are provided with an external threading 106 and are screwable to the slotted outer sleeves 42, namely in particular for temporarily connecting to the angle adjuster 74.

The instrument 72 further comprises a first guide device 114 for guiding a movement of the first coupling device 76 along a section of a circular path 116. The first guide device 114 is partially arranged and formed, respectively, on the main body 80 and comprises two circular arc shaped guide slots 118 and 120 which are arranged concentrically to each other.

In order to fix the first coupling device 76 in a first orientation on the main body 80, a first fixing device 122 is provided, namely in the form of a clamping device 124 having a first clamping element 126 and a second clamping element 128.

The first clamping element comprises a flat plate 128, which bears, on its one side, the receiver 86 and, on its other side, two bolt-shaped connecting members 130, protruding perpendicularly therefrom and penetrating the guide slot 118, which are each provided with a blind hole 132 comprising an internal threading. The second clamping element 128 is also configured in the form of a plate 134 which has two bores 136 that are penetrated by threaded shanks 138 of connecting screws, wherein the threaded shanks 138 are screwed into the blind holes 132.

The two plates 128 and 134 lie on two sides of the main body 80 pointing away from each other. In order to be able to move the two clamping elements 126 and 127 toward each other such that the fixing device 122 assumes the first orientation, a first clamping member 142 is provided with a bolt-shaped threaded shank 144 and a T-shaped head 146. The threaded shank 144 penetrates a bore 148 of the plate 134 as well as a guide slot 120 and is screwed into a threaded bore 150 of the plate 128.

By twisting the clamping member 142 clockwise about its longitudinal axis, the plates 128 and 134 are pulled against each other and clamp the main body 80 between them. If one twists the first clamping member 142 counter-clockwise, then the plates 128 and 134 are released just so far that the first fixing device 122 is pivotable relative to the main body 80 about a pivotal axis which is defined by the curvature of the guide slots 118 and 120. As already outlined, this pivotal axis ideally runs through the midpoint 28.

The first clamping member 142 is configured in the form of a clamping screw 143. This is able to be brought from an adjusting position, in which the clamping device 124 is moveable relative to the main body 80, into a clamping position, in which the clamping device 124 is immovably fixed relative to the main body 80.

The instrument 72 further comprises a locking device 152 for locking the first coupling device 76 on the main body 80 in a normal positon in which the coupling device longitudinal axes 84 and 94 of the coupling devices 76 and 78 are aligned in parallel to each other.

The locking device 152 comprises a latching connecting device 154 having a moveable first latching member 156 and a second latching member 158 which is formed by one of the two connecting members 130. In the exemplarily depicted normal position of the locking device 152 in FIG. 11, the first and the second latching member 156, 158 are engaged in a non-positive- and/or positive-locking manner, in a release position they are disengaged.

The first latching member 156 is configured in the form of a latching lever 162 that is mounted on the main body 80 so as to be pivotable about a pivotal axis 160 which runs parallel to longitudinal axes of the connecting members 130. It comprises a bore 164 that is penetrated by a cylindrical bearing pin 166 which is inserted into a through-bore 168 of the main body 80. The latching lever 162 is inserted in a latching lever recess 170 and is held in the normal position in a pretensioning manner, namely with a spring element 172 in the form of a coil spring configured as a pressure spring, which is inserted into a blind hole bore 174, whose longitudinal axis runs transversely to the pivotal axis 160, and which presses against a proximal end of the latching lever 162.

On the other end of the latching lever 162 is arranged a protruding projection 176 which is able to be brought into engagement with the one connecting member 130 in the normal position, and namely in such a way that the projection 176 engages behind the one connecting member 130 which is held in the normal position between the projection 176 and the pivotal axis 160.

For releasing the locking device 152, an actuating face 178 that is provided on the latching lever 172 pointing away from the spring element 172 and having a multitude of transverse grooves may be applied with a releasing force that compresses the spring element 172 and pivots the latching lever 162 about the pivotal axis 160 such that the projection 176 releases the connecting member 130 cooperating therewith in the normal position. Further, if the first clamping device 124 is released, hence it assumes the adjusting position, the first fixing device 122 may thus be moved in the guide slots 118 and 120 about the pivotal axis of the instrument 72.

In order to be able to adjust and display an angle 180 between the coupling device longitudinal axes 84 and 94, a display device 182 is further formed on the angle adjuster 74. It comprises a multitude of angle markings 186 which are formed on a side face 184 of the main body 80 running concentrically to the pivotal axis of the instrument 72 and which are configured in the form of flat narrow grooves.

On the first coupling device 76 is formed a display member 188, namely in the form of a projection 190 which projects from the plate 128 on a side edge thereof and which points to the angle markings 186. A further display element may optionally also be arranged or formed on the second clamping element 127. Thus, in the embodiment of the angle adjuster 74 depicted in the Figures, a display member 192 corresponding to the display member 188 is also arranged on the plate 134.

The angle adjuster 74 further comprises a second guide device 194 for guiding a movement of the second coupling device 78 along a linear path. It is formed and arranged, respectively, on the main body 80 and comprises two guide bodies 196, each having a guide receiver 198 configured in the form of a perforation and which define a joint longitudinal axis 200. The two guide bodies 196 are arranged spaced apart from each other on a side face of the main body 80 that points away from the side face with the angle markings 186.

The second coupling device 78 is arranged on a rod- or shank-shaped guide member 202, namely on an end thereof. The guide member 202 has a non-round, in particular polygonal cross-section, which is formed substantially correspondingly to a cross-section of the guide receivers 198, such that the guide member 202 is displaceable in the guide receiver 198 in parallel to the longitudinal axis 200.

The retaining ring 90 is laterally arranged on the guide member 202, such that the coupling device longitudinal axes 84 and 94 define a common plane that extends perpendicularly to the pivotal axis 160.

In order to fix the second coupling device 78 in a second orientation on the main body 80, the instrument 72 also further comprises a second fixing device 204 that is also configured in the form of a clamping device 206. It comprises a second clamping member 208 for fixing the guide member 202 on the main body 80 in a clamping manner.

The second clamping member 208 is configured in the form of a clamping screw 210 which penetrates a threaded bore 212 on one of the guide bodies 196, the longitudinal axis of the threaded bore 212 running transversely to the longitudinal axis 200. A threaded shank 214 of the clamping screw 210 is screwed into the threaded bore 212 and presses against the guide member 202 with a free shank end 216 in the second orientation.

The guide member 202 has a groove-shaped guide recess 218 which runs parallel to the longitudinal axis 200 and into which the shank end 216 dips. Inner side faces facing each other on the end of the guide recess 218 form end stops 220 that delimit a displacement movement of the guide member 202 relative to the main body 80.

For actuating the second fixing device, the clamping screw 210 comprises a T-shaped head 222, such that a clockwise twisting of the clamping screw 210 may move the shank end 216 in the direction toward the guide member 202 and, in the case of the a counter-clockwise movement, away from the guide member 202.

The functioning of the instrumentarium 10 will subsequently be briefly described by reference to the FIGS. 1 to 17.

In a first step, as depicted schematically in FIG. 1, bone screws 14 of desired quantity are screwed into pedicles of the vertebrae 60. The bone screws 14 are then each coupled to an instrument 38. Using the insertion instrument 46, connecting rods 34 are then inserted in the manner described above into the rod receivers 30 of two or more bone screws 14.

The connecting rods 34 may now each be prefixed to a bone screw 14 using the screwing-in instrument 50 inserted through the outer sleeve 42.

In order to align in the desired manner an angle between longitudinal axes of the instruments 38 that are connected bone screws 14 which are screwed into adjacent vertebrae 60, the connecting rod 34 is, as is depicted schematically in FIG. 1, fixed to a bone screw 14 using the screwing-in instrument 50.

Now the instrument 72 may be coupled to the two instruments 38 in the described manner, namely as is depicted in FIGS. 4 and 5 by sliding the coupling devices 76 and 78 onto the extension sleeves 104 that are connected to the instruments 38.

The angle adjuster 74 is first located in the normal position, so that the coupling device longitudinal axes 84 and 94 are aligned in parallel to each other.

In order to adjust a desired angle 180 between the coupling device longitudinal axes 84 and 94, first the latching lever 162 is actuated by applying the actuation face 178 with an actuating force. The projection 176 then releases the connecting member 130 engaged therewith and the first coupling device 78 may be pivoted relative to the second coupling device 76 and, respectively, be moved along the guidance path defined by the first guide device 114.

The first fixing device 122 is first loosened and the coupling devices 76 and 78 are pivoted so far until the desired angle 180 is readable on the display device 182.

Now the first coupling device 76 may be fixed in the first orientation using the clamping device 124. For this purpose, the clamping screw 143 is twisted clockwise until the clamping device 124 holds the main body 80 between it in a clamping manner.

In case a further distraction of the adjacent vertebrae 60 is necessary, the first and second coupling device 76, 80 may be displaced in the described manner relative to each other in parallel to the longitudinal axis 200 using the second guide device 194. Optionally, the distractor 64 described above may be used, which is directly coupleable to the ends 40 of the instruments 38, in order to move the bone screws 14 away from each other or toward each other in a direction defined by the connecting rod 34.

Any number of bone screws 14 may be tightly screwed to vertebrae 60 in the described manner. Optionally, using the angle adjuster 74, instruments 38 which are coupled to the bone screws 14 that are fixed to the same vertebra 60 may also be aligned relative to each other.

REFERENCE NUMERAL LIST 10 instrumentarium
12 spinal column stabilization system
14 bone screw
16 shank
18 external threading
20 shank longitudinal axis
22 head
24 seating
26 end
28 midpoint
30 rod receiver
32 wall section
34 connecting rod
36 fixing screw
38 instrument
40 end
42 outer sleeve
44 slot
46 insertion instrument
48 end
50 screwing-in instrument
52 tool element
54 tool element receiver
56 ratchet grip
58 torque limiting device
60 vertebra
62 spinal column
64 distractor
66 leg
68 end
70 distraction bracket
72 instrument
74 angle adjuster
76 first coupling device
78 second coupling device
80 main body
82 point of rotation
84 first coupling device longitudinal axis
86 receiver
88 retaining arc
90 retaining ring
92 receiver
94 second coupling device longitudinal axis
96 inner wall
97 inner wall
98 coupling projection
99 coupling projection
100 coupling recess
102 coupling projection
103 wall face
104 extension sleeve
106 externally threaded section
108 end
110 sleeve
112 coupling sleeve
114 first guide device
116 circular path
118 guide slot
120 guide slot
122 first fixing device
124 clamping device
126 first clamping element
127 second clamping element
128 plate
130 connecting member
132 blind hole
134 plate
136 bore
138 threaded shank
140 connecting screw
142 first clamping member
143 clamping screw
144 threaded shank
146 head
148 bore
150 threaded bore
152 locking device
154 latching connecting device
156 first latching member
158 second latching member
160 pivotal axis
162 latching lever
164 bore
166 bearing pin
168 through bore
170 latching lever recess
172 spring element
174 blind hole bore
176 projection
178 actuating face 180 angle
182 display device
184 side face
186 angle marking
188 display member
190 projection
192 display member
194 second guide device
196 guide body
198 guide receiver
200 longitudinal axis
202 guide member
204 second fixing device
206 clamping device
208 second clamping member
210 clamping screw
212 threaded bore
214 threaded shank
216 shank end
218 guide recess
220 end stop
222 head

What is claimed is:

1. Medical instrument for temporarily coupling to at least two shank-shaped or sleeve-shaped instruments, comprising:
   a first coupling device for temporarily coupling to a first shank-shaped or sleeve-shaped instrument,
   a second coupling device for coupling to a second shank-shaped or sleeve-shaped instrument,
   the first coupling device and the second coupling device being arranged or formed so as to be pivotable relative to each other,
   a main body on which the first coupling device is guided and held so as to be pivotable about a point of rotation that is spatially remote from the main body, and
   a first guide device for guiding a movement of the first coupling device along a circular path,
   wherein:
   the first guide device is arranged or formed at least partially on the main body, and
   the first guide device comprises two or more circular arc shaped guide slots arranged concentrically to each other.

2. Medical instrument in accordance with claim 1, wherein at least one of:
   a) the first coupling device and the second coupling device are arranged or formed so as to be displaceable relative to each other, and
   b) the second coupling device is displaceably guided and held on the main body.

3. Medical instrument in accordance with claim 1, wherein at least one of the first coupling device and the second coupling device are configured in the form of a receiver for a shank-shaped or sleeve-shaped instrument, which defines a coupling device longitudinal axis.

4. Medical instrument in accordance with claim 3, wherein at least one of:
   a) the receivers are configured in the form of retaining rings or retaining arcs, and
   b) at least one protruding coupling projection is arranged or formed at the receivers for coupling to a shank-shaped or sleeve-shaped instrument in at least one of a non-positive-locking and positive-locking manner, or
   c) at least one protruding coupling projection is arranged or formed at the receivers for coupling to a shank-shaped or sleeve-shaped instrument in at least one of a non-positive-locking and positive-locking manner,
   wherein the at least one coupling projection is formed projecting from an inner wall face toward the coupling device longitudinal axis.

5. Medical instrument in accordance with claim 1, further comprising a first fixing device for fixing the first coupling device in a first orientation on the main body.

6. Medical instrument in accordance with claim 5, wherein the first fixing device is configured in the form of a clamping device.

7. Medical instrument in accordance with claim 6, wherein:
   a) the clamping device comprises first and second clamping elements that are coupled to each other by connecting members penetrating the at least one guide slot and that comprise a first clamping member for moving the first and second clamping elements toward each other, or
   b) the clamping device comprises first and second clamping elements that are coupled to each other by connecting members penetrating the at least one guide slot and that comprise a first clamping member for moving the first and second clamping elements toward each other,
   wherein at least one of:
   the first clamping member is configured in the form of a clamping screw which at least partially penetrates the at least one guide slot and is able to be brought from an adjusting position into a clamping position and vice versa, and
   the first clamping element comprises or bears the first receiver.

8. Medical instrument for temporarily coupling to at least two shank-shaped or sleeve-shaped instruments, comprising:
   a first coupling device for temporarily coupling to a first shank-shaped or sleeve-shaped instrument,
   a second coupling device for coupling to a second shank-shaped or sleeve-shaped instrument,
   the first coupling device and the second coupling device being arranged or formed so as to be pivotable relative to each other,
   a main body on which the first coupling device is guided and held so as to be pivotable about a point of rotation that is spatially remote from the main body,
   a first guide device for guiding a movement of the first coupling device along a circular path, and
   a first fixing device for fixing the first coupling device in a first orientation on the main body,
   wherein:
   the first guide device is arranged or formed at least partially on the main body,
   the first guide device comprises two or more circular arc shaped guide slots,
   the first fixing device is configured in the form of a clamping device, and
   the clamping device comprises first and second clamping elements that are coupled to each other by connecting members penetrating the at least one guide slot and that comprise a first clamping member for moving the first and second clamping elements toward each other.

9. Medical instrument in accordance with claim 8, wherein the two circular arc shaped guide slots are arranged concentrically to each other.

10. Medical instrument in accordance with claim 8, wherein at least one of:

a) the first clamping member is configured in the form of a clamping screw which at least partially penetrates the at least one guide slot and is able to be brought from an adjusting position into a clamping position and vice versa, and
b) the first clamping element comprises or bears the first receiver.

11. Medical instrument in accordance with claim 8, further comprising a second guide device for guiding a movement of the second coupling device along a linear path.

12. Medical instrument in accordance with claim 11, wherein:
a) the second guide device is formed on the main body and comprises at least one guide receiver, or
b) the second guide device is formed on the main body and comprises two guide receivers, or
c) the second guide device is formed on the main body and comprises at least one guide receiver,
wherein the second coupling device comprises a rod-shaped or shank-shaped guide member which is guided and held in or at the at least one guide receiver, or
d) the second guide device is formed on the main body and comprises two guide receivers,
wherein the second coupling device comprises a rod-shaped or shank-shaped guide member which is guided and held in or at the at least one guide receiver.

13. Medical instrument in accordance with claim 8, further comprising:
a) a first fixing device for fixing the first coupling device in a first orientation on the main body, or
b) a first fixing device for fixing the first coupling device in a first orientation on the main body,
wherein the first fixing device is configured in the form of a clamping device.

14. Medical instrument for temporarily coupling to at least two shank-shaped or sleeve-shaped instruments, comprising:
a first coupling device for temporarily coupling to a first shank-shaped or sleeve-shaped instrument,
a second coupling device for coupling to a second shank-shaped or sleeve-shaped instrument,
the first coupling device and the second coupling device being arranged or formed so as to be pivotable relative to each other,
a main body on which the first coupling device is guided and held so as to be pivotable about a point of rotation that is spatially remote from the main body,
a first guide device for guiding a movement of the first coupling device along a circular path, and
a locking device for locking the first coupling device on the main body in a normal position in which the coupling device longitudinal axes of the at least two coupling devices are aligned in parallel with each other, wherein:
the first guide device is arranged or formed at least partially on the main body, and
the first guide device comprises two or more circular arc shaped guide slots.

15. Medical instrument in accordance with claim 14, wherein:
a) the locking device comprises a latching connecting device having a moveable first latching member and a second latching member, and wherein the first and the second latching member are engaged in at least one of a non-positive-locking and positive-locking manner in the normal position and are disengaged in a release position, or b) the locking device comprises a latching connecting device having a moveable first latching member and a second latching member, and wherein the first and the second latching member are engaged in at least one of a non-positive-locking and positive-locking manner in the normal position and are disengaged in a release position,
wherein the first latching member is configured in the form of a latching lever that is at least one of displaceably and pivotally mounted on the main body and which has a projection or a recess which is engaged in the normal position with a corresponding recess or a corresponding projection on the first coupling device, or
c) the locking device comprises a latching connecting device having a moveable first latching member and a second latching member, and wherein the first and the second latching member are engaged in at least one of a non-positive-locking and positive-locking manner in the normal position and are disengaged in a release position,
wherein the first latching member is configured in the form of a latching lever that is at least one of displaceably and pivotally mounted on the main body and which has a projection or a recess which is engaged in the normal position with a corresponding recess or a corresponding projection on the first coupling device,
wherein the first latching member is mounted so as to be pivotable about a pivotal axis which runs transversely to the coupling device longitudinal axis of at least one of the first and second coupling device, or
(d) the locking device comprises a latching connecting device having a moveable first latching member and a second latching member, and wherein the first and the second latching member are engaged in at least one of a non-positive-locking and positive-locking manner in the normal position and are disengaged in a release position,
wherein the first latching member is configured in the form of a latching lever that is at least one of displaceably and pivotally mounted on the main body and which has a projection or a recess which is engaged in the normal position with a corresponding recess or a corresponding projection on the first coupling device,
wherein the first latching member is mounted so as to be pivotable about a pivotal axis which runs perpendicularly to the coupling device longitudinal axis of at least one of the first and second coupling device.

16. Medical instrument in accordance with claim 14, further comprising a second fixing device for fixing the second coupling device in a second orientation on the main body.

17. Medical instrument in accordance with claim 16, wherein the second fixing device is configured in the form of a clamping device.

18. Medical instrument in accordance with claim 17, wherein the second clamping device comprises at least one second clamping member for fixing the guide member on the main body in a clamping manner.

19. Medical instrument in accordance with claim 18, wherein:
a) the second clamping member is configured in the form of a clamping screw which penetrates the at least one guide receiver and pushes against the guide member in the second orientation with a free shank end of a clamping screw shank, or b) the second clamping member is configured in the form of a clamping screw which penetrates the at least one guide receiver and pushes against the guide member in the second orientation with a free shank end of a clamping screw shank in a region of a groove-shaped guide recess, or c) the second clamping member is configured in the form of a clamping screw which penetrates the at least one guide receiver and pushes against the guide member in the second orientation with a free shank end of a clamping screw shank, wherein the guide recess defines end stops for a displacement movement of the guide member relative to the main body, or d) the second clamping member is configured in the form of a clamping screw which penetrates the at least one guide receiver and pushes against the guide member in the second orientation with a free shank end of a clamping screw shank in a region of a groove-shaped guide recess, wherein the guide recess defines end stops for a displacement movement of the guide member relative to the main body.

20. Medical instrument in accordance with claim 14, wherein at least one of:

a) the first coupling device and the second coupling device are arranged or formed so as to be displaceable relative to each other, and b) the second coupling device is displaceably guided and held on the main body.

21. Medical instrument in accordance with claim 14, wherein at least one of the first coupling device and the second coupling device are configured in the form of a receiver for a shank-shaped or sleeve-shaped instrument, which defines a coupling device longitudinal axis.

22. Medical instrument in accordance with claim 21, further comprising a display device for displaying an angle between the coupling device longitudinal axes of the at least two coupling devices.

23. Medical instrument in accordance with claim 22, wherein:

a) the display device comprises angle markings on the main body, and a display member, arranged or formed on the first coupling device, which points to the angle markings, or b) the display device comprises angle markings on the main body, and a display member, arranged or formed on the first coupling device, which points to the angle markings, wherein the display member is arranged or formed on at least one of the first and second clamping element.

24. Medical instrument in accordance with claim 14, further comprising:

a) a first fixing device for fixing the first coupling device in a first orientation on the main body, or b) a first fixing device for fixing the first coupling device in a first orientation on the main body, wherein the first fixing device is configured in the form of a clamping device.

25. Medical instrumentarium for implanting a spinal column stabilization system, comprising:

at least two shank-shaped or sleeve-shaped instruments, and a medical instrument for temporarily coupling the at least two shank-shaped or sleeve-shaped instruments, said medical instrument comprising:

a first coupling device for temporarily coupling to a first shank-shaped or sleeve-shaped instrument, and a second coupling device for coupling to a second shank-shaped or sleeve-shaped instrument, the first coupling device and the second coupling device being arranged or formed so as to be pivotable relative to each other, a main body on which the first coupling device is guided and held so as to be pivotable about a point of rotation that in particular is spatially remote from the main body, and a first guide device for guiding a movement of the first coupling device along a circular path, wherein:

the first guide device is arranged or formed at least partially on the main body, and the first guide device comprises two or more circular arc shaped guide slots arranged concentrically to each other.

\* \* \* \* \*

UNITED STATES PATENT AND TRADEMARK OFFICE
CERTIFICATE OF CORRECTION

| | |
|---|---|
| PATENT NO. | : 10,588,673 B2 |
| APPLICATION NO. | : 15/990966 |
| DATED | : March 17, 2020 |
| INVENTOR(S) | : Fischer et al. |

Page 1 of 1

It is certified that error appears in the above-identified patent and that said Letters Patent is hereby corrected as shown below:

In the Claims
Column 20, Line 31:
"of rotation that in particular is spatially remote from"
Should read:
-- of rotation that is spatially remote from --

Signed and Sealed this
Twenty-third Day of June, 2020

Andrei Iancu
*Director of the United States Patent and Trademark Office*